United States Patent
Otawara

(10) Patent No.: US 6,827,683 B2
(45) Date of Patent: Dec. 7, 2004

(54) ENDOSCOPE SYSTEM AND MEDICAL TREATMENT METHOD

(75) Inventor: Takashi Otawara, Hachioji (JP)

(73) Assignee: Olympus Corporation, Tokyo (JP)

( * ) Notice: Subject to any disclaimer, the term of this patent is extended or adjusted under 35 U.S.C. 154(b) by 142 days.

(21) Appl. No.: 10/269,421

(22) Filed: Oct. 11, 2002

(65) Prior Publication Data

US 2003/0073955 A1 Apr. 17, 2003

(30) Foreign Application Priority Data

Oct. 12, 2001  (JP) ........................................ 2001-315750

(51) Int. Cl.[7] ................................................ A61B 1/04
(52) U.S. Cl. ........................ 600/123; 600/104; 600/106; 600/153
(58) Field of Search ................................ 600/123, 153, 600/104, 106, 107, 114; 606/106, 205, 206

(56) References Cited

U.S. PATENT DOCUMENTS

| | | | | |
|---|---|---|---|---|
| 5,386,818 A | * | 2/1995 | Schneebaum et al. | ...... 600/104 |
| 5,820,546 A | * | 10/1998 | Ouchi | ........................ 600/123 |
| 5,899,850 A | * | 5/1999 | Ouchi | ........................ 600/104 |
| 5,921,971 A | | 7/1999 | Agro et al. | |
| 5,938,586 A | * | 8/1999 | Wilk et al. | .................. 600/123 |

FOREIGN PATENT DOCUMENTS

JP         2002-34905         2/2002

* cited by examiner

Primary Examiner—Beverly M. Flanagan
(74) Attorney, Agent, or Firm—Scully, Scott, Murphy & Presser

(57) ABSTRACT

An endoscope system comprises: an endoscope main body having an insertion portion in which a lumen is formed, the insertion portion having a proximal end and a distal end, a distal end opening of the lumen being provided to the distal end of the insertion portion, and a proximal end opening of the lumen being provided to the proximal end of the insertion portion; a first fixing member provided to the distal end of the insertion portion, capable of selecting between a fixed state for fixing the distal end portion of a linear member inserted into the lumen and a released state thereof in the distal end portion of the insertion portion; a second fixing member provided to the proximal end of the insertion portion, capable of selectively fixing the proximal end portion of the linear member inserted into the lumen in the proximal end of the insertion portion; and a tubular member having a proximal end, a distal end, and a lumen running therebetween, and removably inserted into the lumen, wherein a slit is formed from the proximal end of the tubular member towards the distal end thereof.

40 Claims, 22 Drawing Sheets

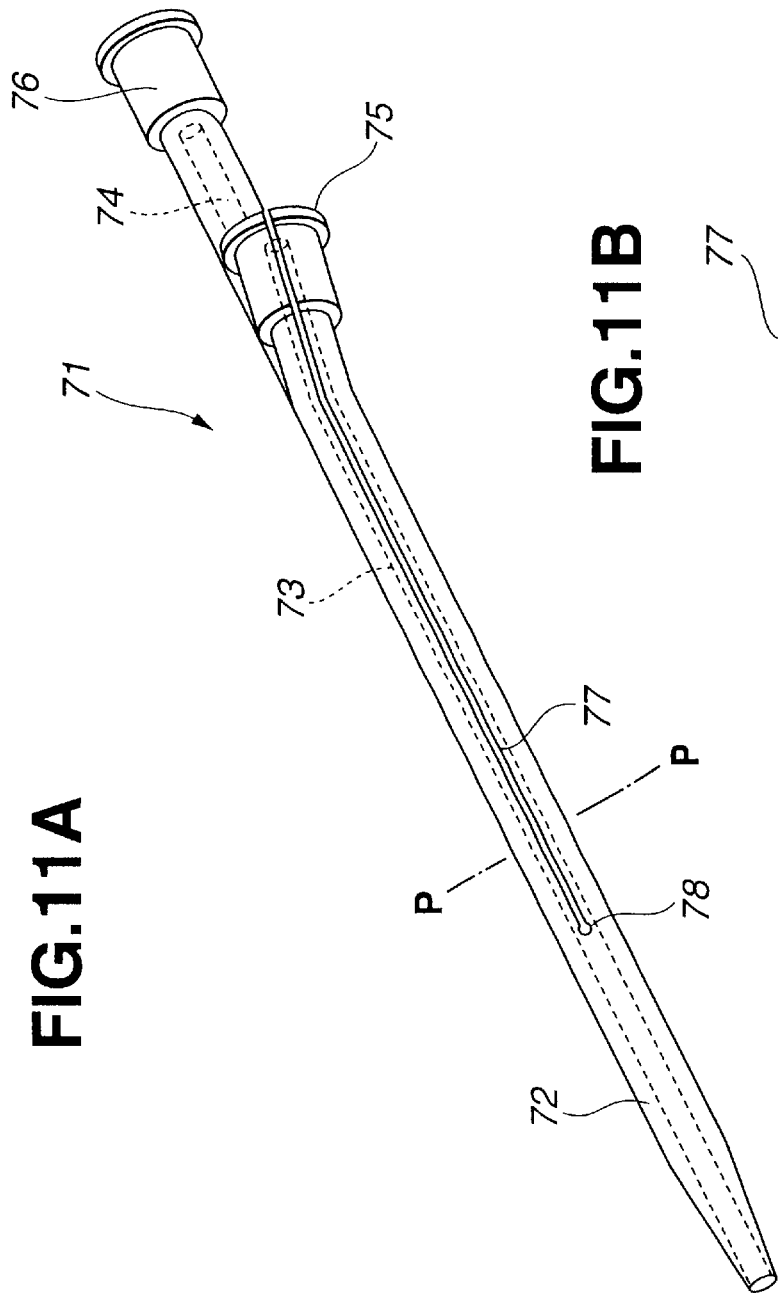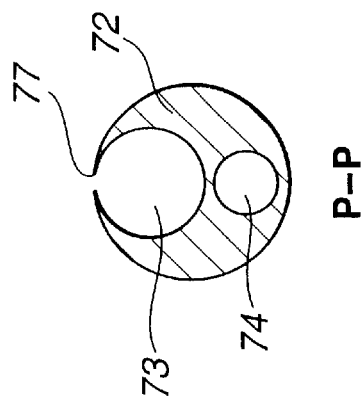

FIG.31
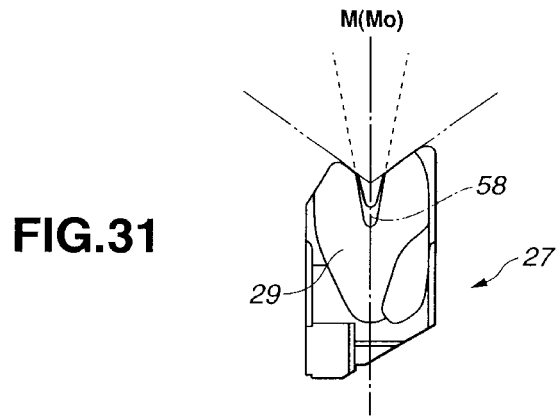
FIG.32A FIG.32B
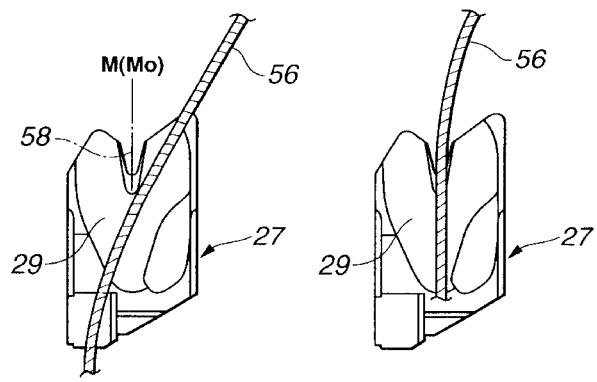
FIG.33
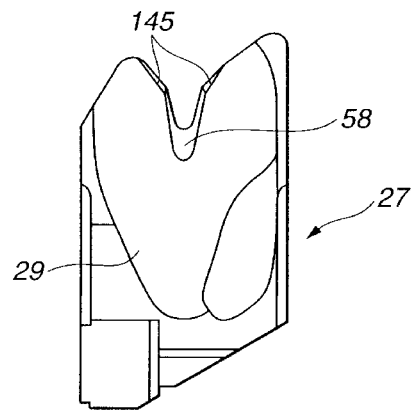

ENDOSCOPE SYSTEM AND MEDICAL TREATMENT METHOD

This application claims benefit of Japanese Application No. 2001-315750 filed in Japan on Oct. 12, 2001, the contents of which are incorporated by this reference.

BACKGROUND OF THE INVENTION

1. Field of the Invention

The present invention relates to an endoscope system used in the diagnosis and treatment of diseases of the gastrointestinal or pancreatobiliary duct systems, and to a medical treatment method.

2. Description of the Related Art

The use of endoscopic treatments has recently been increasing for some diseases occurring in the gastrointestinal or pancreatobiliary duct systems.

For example, endoscope systems used for the abovementioned pancreatobiliary duct systems include diagnostic procedures for contrast imaging of biliary or pancreatic ducts using an endoscope, as well as treatments and the like for retrieving gallstones that exist in the common bile duct and elsewhere by means of a balloon or gripping implement passed through the treatment instrument threading channel of an endoscopic treatment system.

These treatments are performed in the pancreatic duct, bile duct, hepatic duct, and the like usually by passing the end of an endoscope insertion portion up to the vicinity of the duodenal papilla, and then selectively inserting a catheter or similar treatment instrument passed through the endoscope treatment instrument threading channel into the pancreatic duct, bile duct, or hepatic duct with a guidewire under X-ray illumination.

The abovementioned guidewire used in the pancreatobiliary duct system may be about 400 cm in length.

In U.S. Pat. No. 5,921,971, a bile duct catheter is proposed for facilitating exchanging of a treatment instrument.

The bile duct catheter according to U.S. Pat. No. 5,921,971 extends an opening in a longitudinal direction between the distal and proximal sections of the guidewire lumen in the catheter shaft.

Specifically, the bile duct catheter having a firfixening at the front end of the guidewire lumen, and a second opening communicated with the first opening on the proximal side, and a treatment instrument for which the guidewire is used as a guide inserts and removes in a state in which the guidewire is fixed by being held down when extended from a slit.

Endoscope systems in which a mini-scope, ultrasound probe, or the like is threaded from the treatment instrument threading channel to perform observation and treatment are also used on an increasing scale, primarily in cases involving the pancreatobiliary system.

In such cases, the endoscope systems are operated such that a mini-scope, ultrasound probe, or other component threaded through the treatment instrument threading channel is elevated toward the desired affected area with the aid of a treatment instrument elevator fitted to the distal section of the endoscope insertion portion.

An endoscope system featuring the catheter thus configured requires that the following two operations performs exchanging of the treatment instrument when the treatment instrument is exchanged in a situation in which, for example, the tip of the guidewire is inserted into the duodenal papilla, by inserting the guidewire to the same degree of travel while the treatment instrument is withdrawn from the treatment instrument threading channel of the endoscope, or by withdrawing the guidewire to the same degree of travel in the same manner while the treatment instrument is inserted into the treatment instrument threading channel.

An endoscope system comprising a treatment instrument elevator in which a guidewire fixing slit is formed on the apex of the guide surface thereof is proposed in Japanese Patent Application Laid-open No. 2002-34905. The guidewire is usually rigid; but because of the length thereof, the distal end of the guidewire protruding from the treatment instrument threading channel does not necessarily extend straight out from the treatment instrument threading channel.

SUMMARY OF THE INVENTION

It is desirable if there were an endoscope system which can facilitate the exchanging of a treatment instrument.

According to a first aspect of the present invention, an endoscope system comprises an endoscope main body, a first fixing member, a second fixing member and a tubular member. The endoscope main body has an insertion portion in which a lumen is formed and the insertion portion has a proximal end and a distal end. A distal end opening of the lumen is provided to the distal end of the insertion portion and a proximal end opening of the lumen is provided to the proximal end of the insertion portion. The first fixing member provided to the distal end of the insertion portion is capable of selecting between a fixed state for fixing the distal end portion of a linear member inserted into the lumen and a released state thereof in the distal end portion of the insertion portion. The second fixing member provided to the proximal end of the insertion portion is capable of selectively fixing the proximal end portion of the linear member inserted into the lumen in the proximal end of the insertion portion. And the tubular member has a proximal end, a distal end, and is a lumen running therebetween, and is removably inserted into the lumen. A slit is formed from the proximal end of the tubular member towards the distal end thereof.

According to a second aspect of the present invention, a medical treatment method comprises the following steps. The method includes a step for inserting a first treatment instrument into the lumen of the endoscope insertion portion and placing the distal end of the first treatment instrument in the body cavity. The method further includes a step for placing a guidewire in the lumen of the first treatment instrument, a step for pulling the proximal end portion of the guidewire diametrically from the lumen of the first treatment instrument after the distal end of the guidewire inserted into the first treatment instrument is placed in the body cavity, and a step for fixing the portion of the proximal end of the guidewire pulled from the first treatment instrument at the proximal end of the endoscope lumen, and a step for pulling the first-treatment instrument towards the proximal end of the insertion portion. The method further includes a step for fixing the distal end portion of the guidewire at the distal end of the endoscope insertion portion after the distal end of the first treatment instrument is positioned within the insertion portion of the endoscope, a step for releasing the fixing of the guidewire in the proximal end of the endoscope insertion portion, and a step for pulling the first treatment instrument from the proximal end opening of the endoscope insertion portion.

Other characteristics and merits of the present invention will be made adequately clear by the following description.

BRIEF DESCRIPTION OF THE DRAWINGS

The accompanying drawings, which are incorporated in and constitute a part of the specification, illustrate exemplary embodiments of the invention, and together with the general description above and the detailed description of illustrative embodiments given below, serve to explain the principles of the invention.

FIG. 11A is a diagram depicting the guidewire fixing treatment instrument assembled with the endoscope of the endoscope system according to the first embodiment of the present invention;

FIG. 11B is a cross-sectional diagram along the cutting-plane line P—P in FIG. 11A;

FIG. 31 is a diagram depicting the guide surface of the treatment instrument elevator in the endoscope system according to the sixth embodiment of the present invention;

FIG. 32A is a diagram depicting the operation of the guide surface of the treatment instrument elevator in a conventional endoscope system;

FIG. 32B is a diagram depicting the operation of the guide surface of the treatment instrument elevator in the endoscope system according to the sixth embodiment of the present invention;

FIG. 33 is a diagram depicting the guide surface of the treatment instrument elevator in the endoscope system according to the sixth embodiment of the present invention;

DETAILED DESCRIPTION OF THE PREFERRED EMBODIMENTS

Embodiments of the present invention will be described hereafter with reference to the figures.

(First Embodiment)

A detailed description will hereafter be give of the first embodiment of the present invention, with reference to FIGS. 1 through 14.

Figure 1:
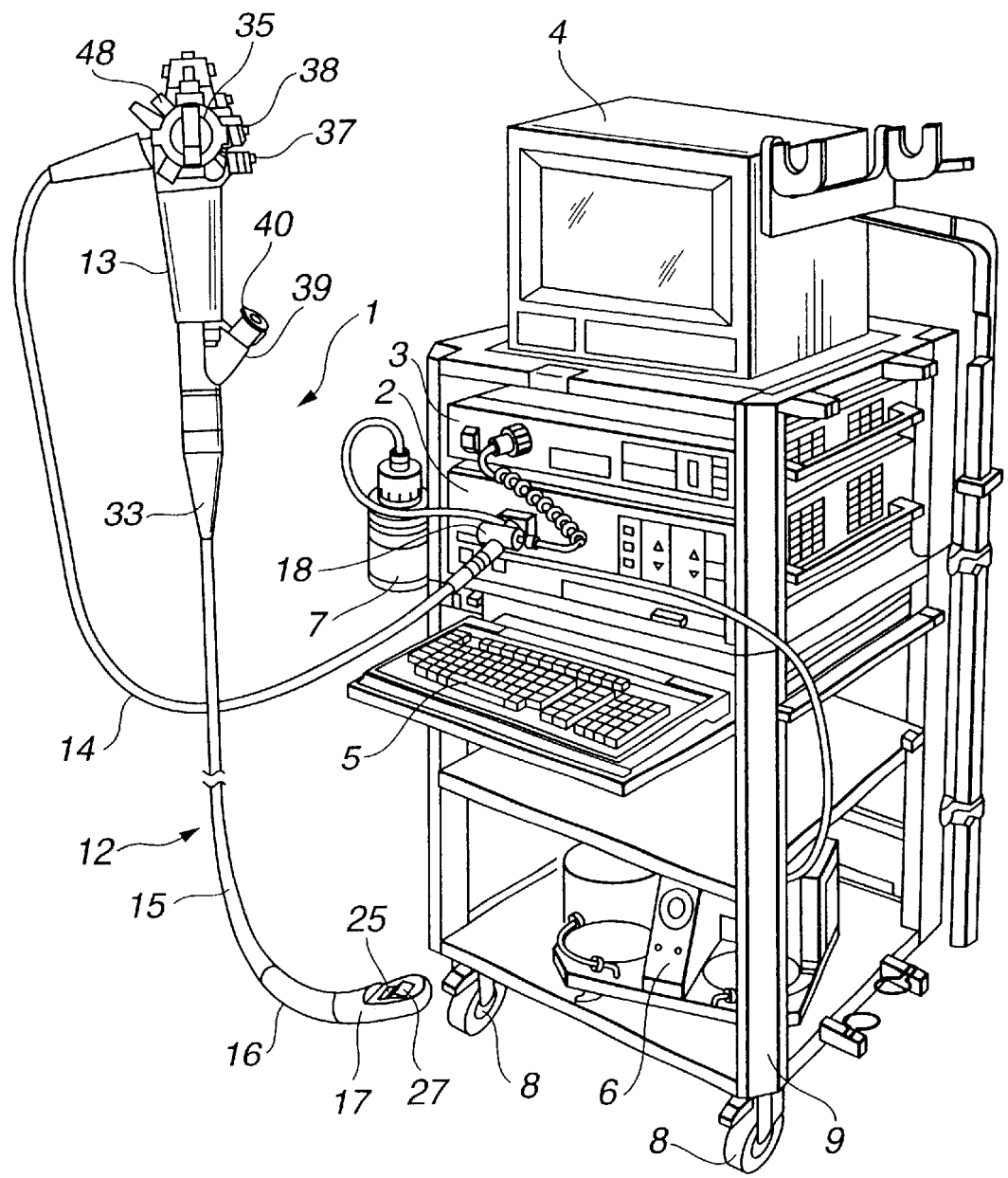
FIG. 1 is a perspective view depicting the overall structure of the endoscope system according to the first embodiment of the present invention.

The overall structure of the endoscope system according to the present invention will first be described using FIG. 1. The endoscope 1 comprises a slender insertion portion 12 inserted into the body cavity, an operating portion 13, and a universal cord 14. The insertion portion 12 is composed of the constituent parts comprising a flexible tube 15, a flexure 16, and a tip 17. The endoscope 1 is also provided with an insertion portion protecting member 33 for protecting the insertion portion 12 at a location in which the insertion portion 12 and the operating portion 13 are connected together.

One end of the universal cord 14 is connected to the aforementioned operating portion 13. A connector 18 is provided to the other end of the universal cord 14. The connector 18 is provided with a light guide tube and electrical contact, and is connected with a light source apparatus 2 and an image processing apparatus 3 (external devices).

These external devices, consisting of a monitor 4, input keyboard 5, suction pump apparatus 6, irrigation bottle 7, and the like in addition to the light source apparatus 2 and image processing apparatus 3, are installed on a rack 9 equipped with carriers 8.

Figure 2:
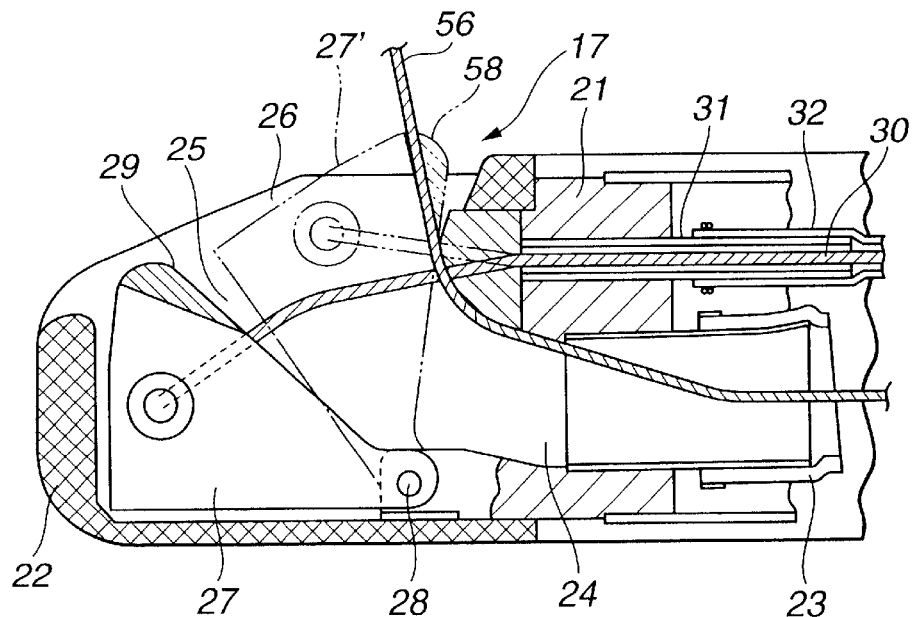
FIG. 2 is a cross-sectional diagram depicting the structure of the tip of the endoscope insertion portion of the endoscope system according to the first embodiment of the present invention.
Figure 12A:
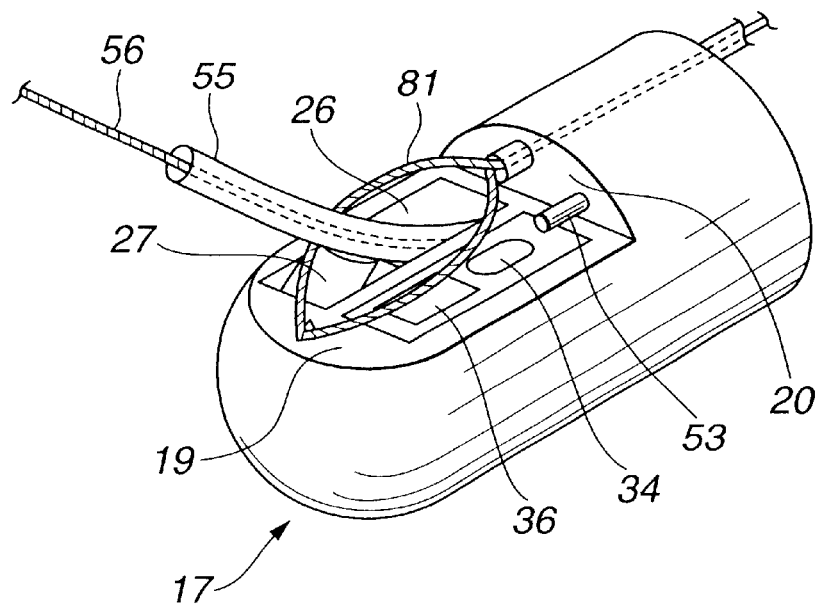
FIG. 12A is a diagram depicting the first additional embodiment of the tip of the endoscope insertion portion of the endoscope system according to the first embodiment of the present invention.

FIGS. 2 and 12A will next be used to describe the configuration of the tip 17 of the endoscope 1.

As depicted first in FIG. 12A, a concave depressed slit 19 cut on one side of the outer circumferential surface is formed in the outer circumferential surface of the tip 17.

A channel opening 26 is provided on one side of the slit 19. An objective lens 34 of an observation optical system and an illuminating lens 36 of an illuminating optical system are disposed next to the channel opening 26.

The tip 17 is also provided with a nozzle 53 for air and water delivery protruding from the back wall surface 20 of the slit 19. A stream of water, air, or the like is ejected towards the outer surface of the objective lens 34 from the nozzle 53 to clean the lens surface.

A guide catheter 55 (hereinafter described) and a guidewire 56 threaded through the inside of the guide catheter 55 protrude from the channel opening 26. The channel opening 26 is furthermore provided with a treatment instrument elevator 27 for elevating the guide catheter 55.

The internal structure of the tip 17 will next be described in detail using FIG. 2.

The tip 17 comprises a rigid tip 21 as the main body of the tip, and a tip cover 22 for covering the perimeter of the rigid tip 21, formed using a nonconductive member such as resin or the like. The tip cover 22 is fastened to the rigid tip 21 with an adhesive or the like.

The rigid tip 21 is formed such that communication is ensured with the treatment instrument threading channel 23, which acts as a guide path for the threading through of treatment instruments, and is provided with an insertion guide passage 24 for guiding the insertion of a treatment instrument or the like towards the tip. The insertion guide passage 24 is provided with an accommodation space 25, which is a space formed by the rigid tip 21 and the tip cover 22, on the tip side thereof.

The channel opening 26 is formed such that the tip opening of the treatment instrument threading channel 23 is composed of an opening in the accommodation space 25.

The accommodation space 25 also houses a treatment instrument elevator 27 for raising to the desired location a treatment instrument (not shown) such as forceps, a catheter, or the like inserted into the interior thereof through the treatment instrument threading channel 23.

One end of the treatment instrument elevator 27 is attached so as to pivot around the elevator turning support 28 provided to the rigid tip 21. The elevator turning support 28 is located below the tip opening of the insertion guide passage 24.

The treatment instrument elevator 27 is mounted such that the portion facing the other tip is free to turn up and down inside the accommodation space 25.

A guide plane 29 for guiding a treatment instrument is formed from a groove with a substantially V-shaped cross-section formed in the treatment instrument elevator 27 to provide a connection with the insertion guide passage 24.

An elevator wire 30 is connected to the treatment instrument elevator 27. The opposite end of the elevator wire 30 is guided to the operating portion 13 through a guide tube 32 and the guide pipe 31 threaded into the insertion portion 12, and is connected to the hereinafter described elevator operating mechanism 41.

The treatment instrument elevator 27 is structured so as to be raised to the position of the treatment instrument elevator 27' (depicted by the two-dot chained line in the figure) about the elevator turning support 28 as the elevator wire 30 is pulled.

The fixing operation of the guidewire 56 by the treatment instrument elevator 27 will be described using FIG. 5A.

The treatment instrument elevator 27 is rotated about the elevator turning support 28 by the pulling action of the elevator wire 30 in the clockwise direction in the figure.

At this time, the guidewire 56 is raised in the direction of the arrow P in the figure and pushed against the rigid tip 21 as the treatment instrument elevator 27 is rotated clockwise when the guidewire is threaded through the guide plane 29 of the treatment instrument elevator 27.

Because it is formed from a rigid material, the guidewire 56 tends to remain straight when pushed against the rigid tip 21, creating a reactive force in the direction of the arrow Fr in the figure.

Figure 5A:
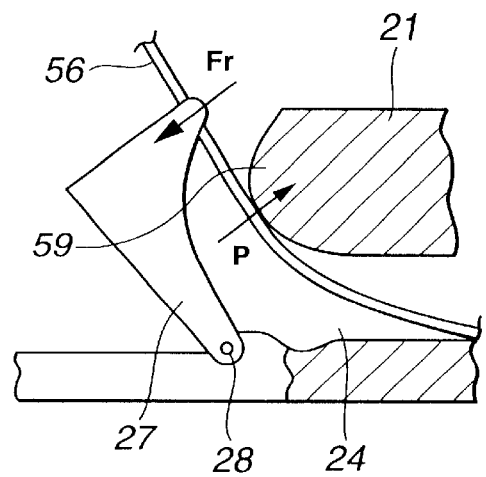
FIG. 5A is a diagram depicting the fixing of the guidewire by means of the treatment instrument elevator.
Figure 5B:
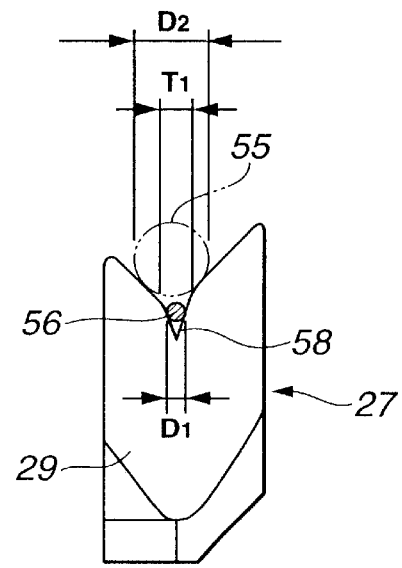
FIG. 5B is a diagram depicting the substantially V-shaped guidewire catch groove formed in the guide plane of the treatment instrument elevator.

By means of this reactive force, the guidewire 56 is pressed and firmly secured against the guidewire catch groove 58 depicted in FIG. 5B (as a groove whose cross-section is substantially V-shaped) and formed in the guide plane 29 of the treatment instrument elevator 27. In other words, the treatment instrument elevator 27 and rigid tip 21 comprise a first guidewire securing means for securing the rigid guidewire 56.

As depicted in FIG. 5B, a groove whose cross-section is substantially V-shaped is formed in the guide plane 29 of the treatment instrument elevator 27, and the slit-shaped guidewire catch groove 58 is formed as a first guidewire securing means for releasably securing the guidewire 56 in the bottom of the V-shaped groove.

The guidewire catch groove 58 has two opposing wall surfaces having a width such that contact occurs only with the outer periphery of the guidewire 56. Furthermore, the relationship between the slit width (groove width) T1 of the orifice, the wire diameter D1 of the guidewire 56, and the external diameter D2 of the treatment instrument, guide catheter 55, or the like in the guidewire catch groove 58 is established such that $D1 \leq T1 < D2$.

A groove having a cross-section whose width narrows in a tapered shape towards the bottom in a substantial V-shape is preferable for the guidewire catch groove 58. Fixing is possible within a substantial V-shape opening angle of 10°–60°, which is selected according to an appropriate external diameter for the guidewire 56.

Figure 5C:
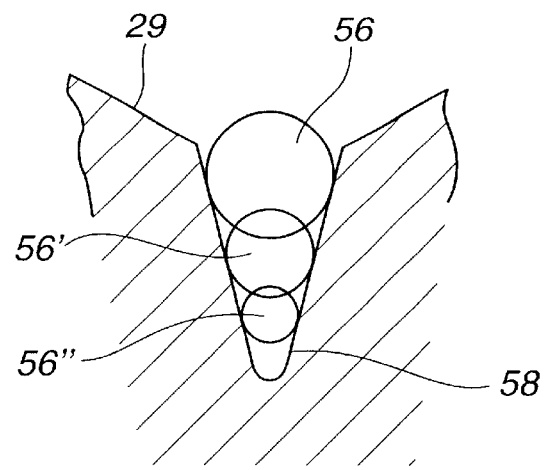
FIG. 5C is a magnified view of the guidewire catch groove in FIG. 5B.

As depicted in FIG. 5C, the opening angle of the guidewire catch groove 58 is set to a sharp angle within the abovementioned range, such that the points of contact with the guidewire catch groove 58 vary for guidewires 56, 56', or 56" with different external diameters. By this means, the treatment instrument elevator 27 can be adapted to fixing a plurality of types of guidewires 56 in a single guidewire catch groove 58.

The operating portion 13 (see FIG. 1) of the endoscope 1 is provided with a bending operator portion 35 for bending the flexure 16 of the insertion portion 12 up, down, and side to side; an air/water emission button 37 for selectively emitting a jet of vapor or liquid to the nozzle 53 for ejecting a stream of water, air, or the like towards the outer surface of the objective lens 34 of the tip 17 and performing cleaning thereof; a suction operator button 38 for selectively retrieving mucous or the like from within the body cavity through the treatment instrument threading channel 23 that is communicated with the tip 17; a forceps opening 39 leading to the treatment instrument threading channel 23 and a forceps fixing 40 for the forceps opening 39; and an elevation operator knob 48.

The internal structure relating to the elevation operator knob 48 of the operating portion 13 will next be described using FIGS. 3 and 4.

The elevator operating mechanism 41 for operating the elevator wire 30 for controlling the treatment instrument elevator 27 is housed within the operating portion 13.

A wire fixing member 42 formed from metal or another hard rod-shaped material and attached integrally with solder or the like to the proximal section of the elevator wire 30, and a link member 44 formed from a rigid block of metal or the like at the proximal section of the wire fixing member 42 are secured to the elevator operating mechanism 41.

An insertion hole 52 is formed in the wire fixing member 42 of the link member 44, and the proximal section of the wire fixing member 42 is inserted into the insertion hole 52 of the link member 44.

An insertion hole 52 into which the proximal portion of the wire fixing member 42 is inserted is formed in the link member 44. The wire fixing member 42 is designed such that the entire area in which the catch groove 43 is formed in the proximal portion thereof is inserted into the insertion hole 52 of the link member 44.

The link member 44 is also provided with a female screw 45 into which the fixing screw 46 of the wire fixing member 42 is screwed. The distal portion of the fixing screw 46 screwed into the female screw 45 is fixed in an inserted condition in the catch groove 43 of the wire fixing member 42. By this means, the wire fixing member 42 is connected to the link member 44 in a stable condition.

Furthermore, the inside of the operating portion 13 is provided with a guide member 47 which acts as a base. The link member 44 is disposed so as to be able to advance and retreat in the longitudinal direction of the guide member 47. Also, one end of an arm 49 of the link member 44 is rotatably connected by the link axis 50, which is a rod-shaped axis member.

The end of this link axis 50 opposite the end facing the guide member 47 is engaged by an engaging member 51 formed from a C or E-type retaining ring or the like.

Furthermore, the other end of the arm 49 is connected to the elevation operator knob 48 provided adjacent to the bending operator portion 35.

In this arrangement, the elevator wire 30 is pulled via the arm 49, link member 44, and wire fixing member 42 (in that order), and the aforementioned treatment instrument elevator 27 is raised about the elevator turning support 28 by the operation of the elevation operator knob 48.

Consequently, the guide catheter 55 and the guidewire 56 are raised by the treatment instrument elevator 27 when threaded through the treatment instrument threading channel 23 and guided towards the outside from the channel opening 26.

The aforementioned operating portion 13 is provided with a second guidewire fixing portion 60 (not shown in FIG. 1) as a second guidewire fixing means for fixing the guidewire 56 on the side of the forceps opening 39.

Figure 6:
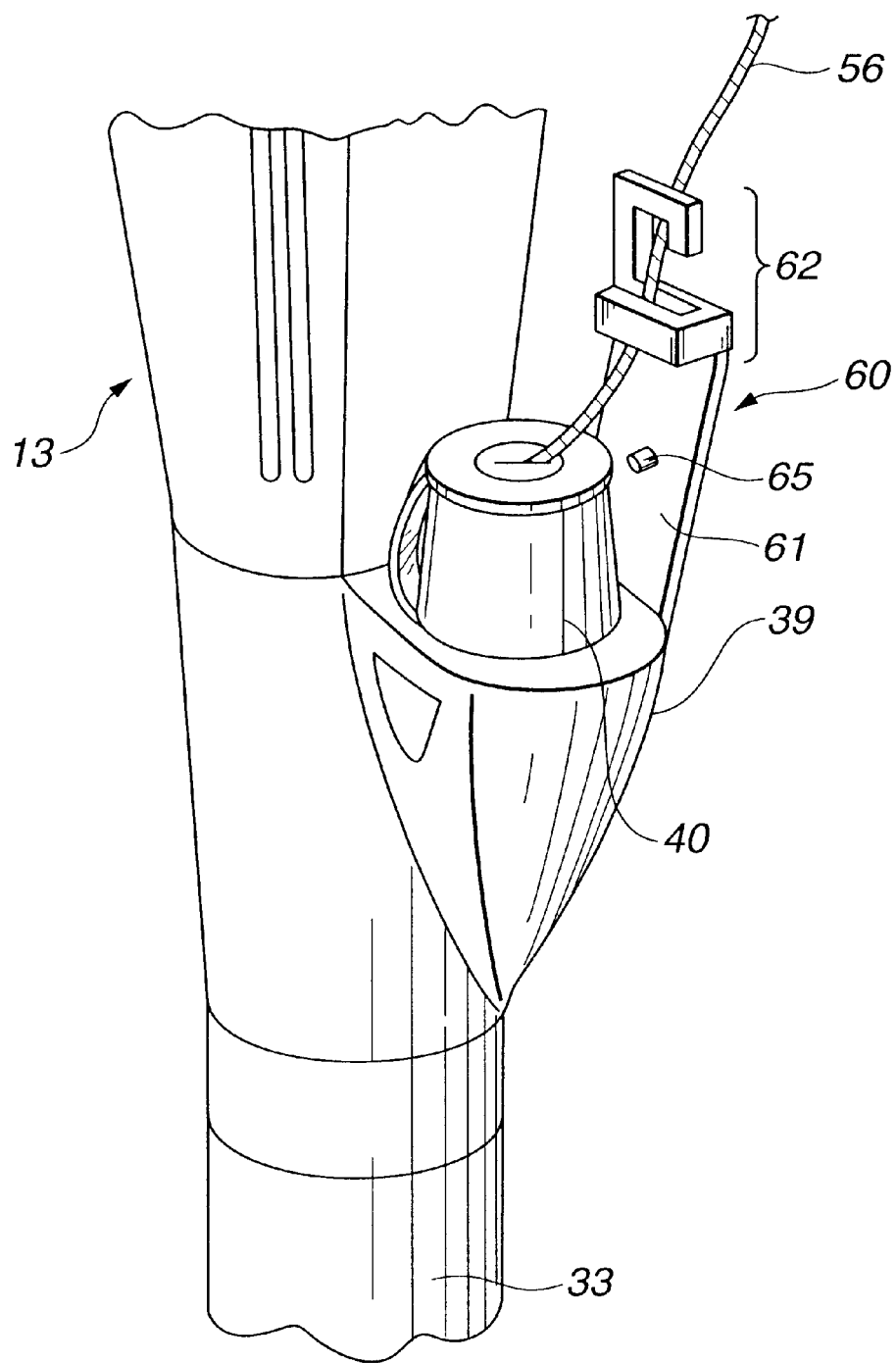
FIG. 6 is a perspective view depicting the forceps opening provided to the operating portion of the endoscope in the endoscope system according to the first embodiment of the present invention.

The structure of this second guidewire fixing portion 60 will be described using FIGS. 6 and 7.

The second guidewire fixing portion 60 comprises a main body portion 61 and a guidewire gripping portion 62. The bottom end of the main body portion 61 has a rotating shaft 63 and is rotatably secured to the forceps opening 39 of the aforementioned endoscope 1.

The second guidewire fixing portion 60 is usually situated in location A of the second guidewire fixing portion 60' (depicted by the bulleted line in FIG. 7 and directed parallel to the insertion portion 12) when the guidewire 56 used in medical applications is not threaded from the forceps opening 39 through the treatment instrument threading channel 23 of the insertion portion 12.

The guidewire 56 is threaded from the forceps opening 39 through the treatment instrument threading channel 23 of the insertion portion 12, and the second guidewire fixing portion 60 can be selectively and temporarily latched in the location B in the figure, which is substantially parallel to the direction extending towards the treatment instrument threading channel 23 from the forceps opening 39 when the guidewire 56 is fixed.

The main body portion 61 is provided with an engaging prong 65 in order to provide this temporary latching capability. The forceps opening 39 is also provided with a catch groove 64a in the location (location B in FIG. 7) in which the main body portion 61 of the second guidewire fixinq portion 60 is engaged when the guidewire 56 is fixed. Furthermore, the forceps opening 39 is provided with a catch groove 64b in the location (location A in FIG. 7) in which the main body portion 61 of the second guidewire fixing portion 60 is usually engaged in the insertion portion protecting member 33 during disease cases.

The engaging prong 65 may be provided to the endoscope 1, and the catch grooves 64 may be provided to the second guidewire fixing portion 60.

Figure 8A:
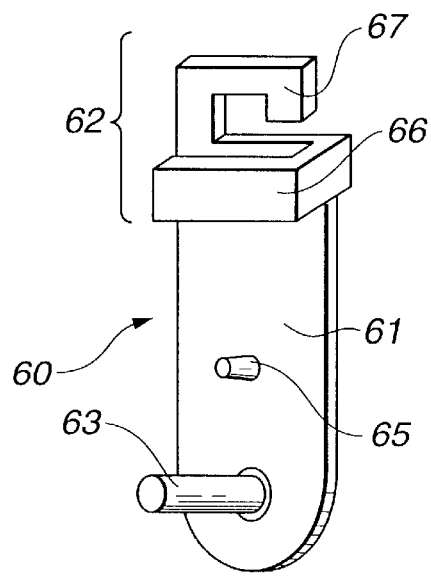
FIG. 8A is a diagram depicting the external structure of the second guidewire locking member provided to the forceps opening of the endoscope operating portion in the endoscope system according to the first embodiment of the present invention.
Figure 8B:
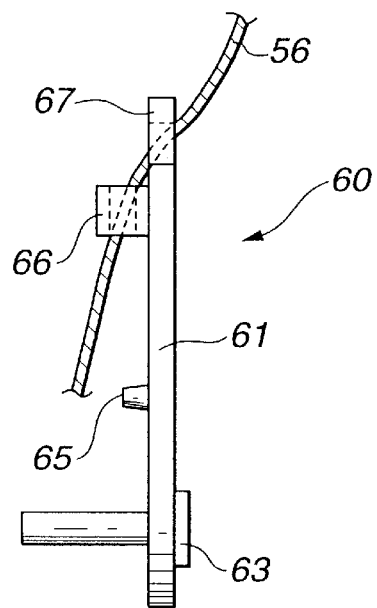
FIG. 8B is a lateral surface view of FIG. 8A.

FIGS. 8A and 8B will next be used to describe the structure of the gripping portion 62 of the second guidewire fixing portion 60, and the manner in which the guidewire 56 is fixed/locked by the gripping portion 62 of the second guidewire fixing portion 60.

As depicted in FIG. 8A of the second guidewire fixing portion 60, an L-shaped first hook 66 is formed protruding towards the forceps opening 39 in a location opposite the rotating shaft 63 of the main body portion 61. A substantially elbow-shaped second hook 67 is formed above the first hook 66 on the same surface as the main body portion 61.

The guidewire 56 is threaded between the main body portion 61 and the first hook 66 as depicted in FIG. 8B, and is furthermore fixed and locked by being threaded through the inside of the elbow-shape of the aforementioned second hook 67.

Because the guidewire 56 is formed from a rigid material, the guidewire 56 tends to remain straight when pressed against the space between the main body portion 61 and second hook 67, and against the second hook 67; and friction occurs between the main body portion 61, first hook 66, second hook 67, and the guidewire 56 such that the guidewire 56 can be fixed and locked.

Figure 9A:
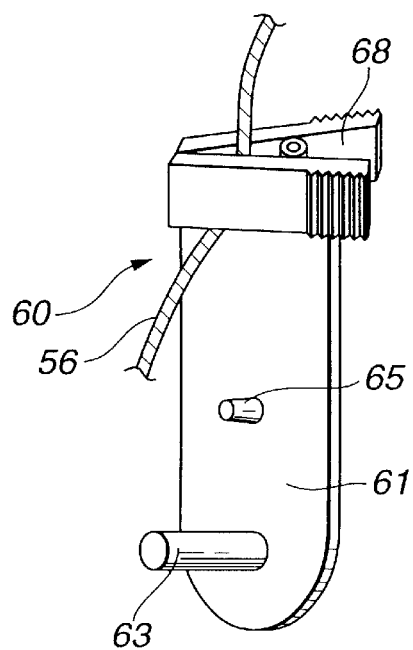
FIG. 9A is a diagram depicting another embodiment of the second guidewire locking member provided to the forceps opening of the endoscope operating portion in the endoscope system according to the first embodiment of the present invention.
Figure 9B:
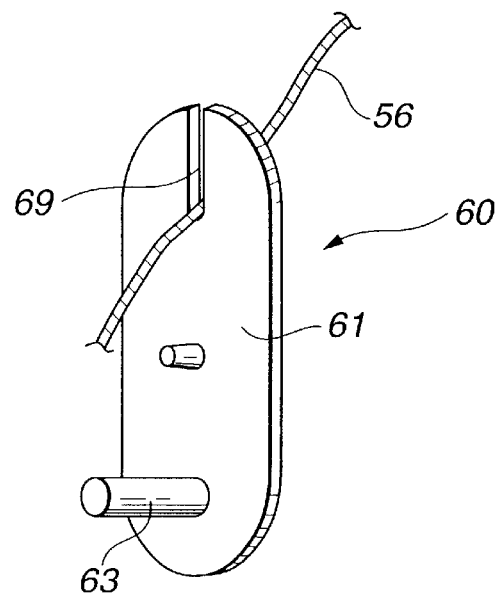
FIG. 9B is a diagram depicting another embodiment of the second guidewire locking member provided with a slit instead of the scissor-shaped clip member in FIG. 9A.

The gripping portion 62 of the aforementioned second guidewire fixing portion 60 was described as comprising a first hook 66 and a second hook 67. However, a scissor-shaped clip member 68 as depicted in FIG. 9A (or a slit 69 or the like as depicted in FIG. 9B) may be provided to the main body portion 61 of the second guidewire fixing portion 60 to yield a configuration capable of temporarily fixing the guidewire 56.

The second guidewire fixing portion 60 may also have another structure that can be attached to and released from the forceps opening 39 of the endoscope 1.

The guidewire fixing treatment instrument 70 used when threading the guidewire 56 from the forceps opening 39 of the endoscope 1 through the treatment instrument threading channel 23 of the insertion portion 12 will next be described using FIGS. 10, 11A, and 11B.

Figure 10:
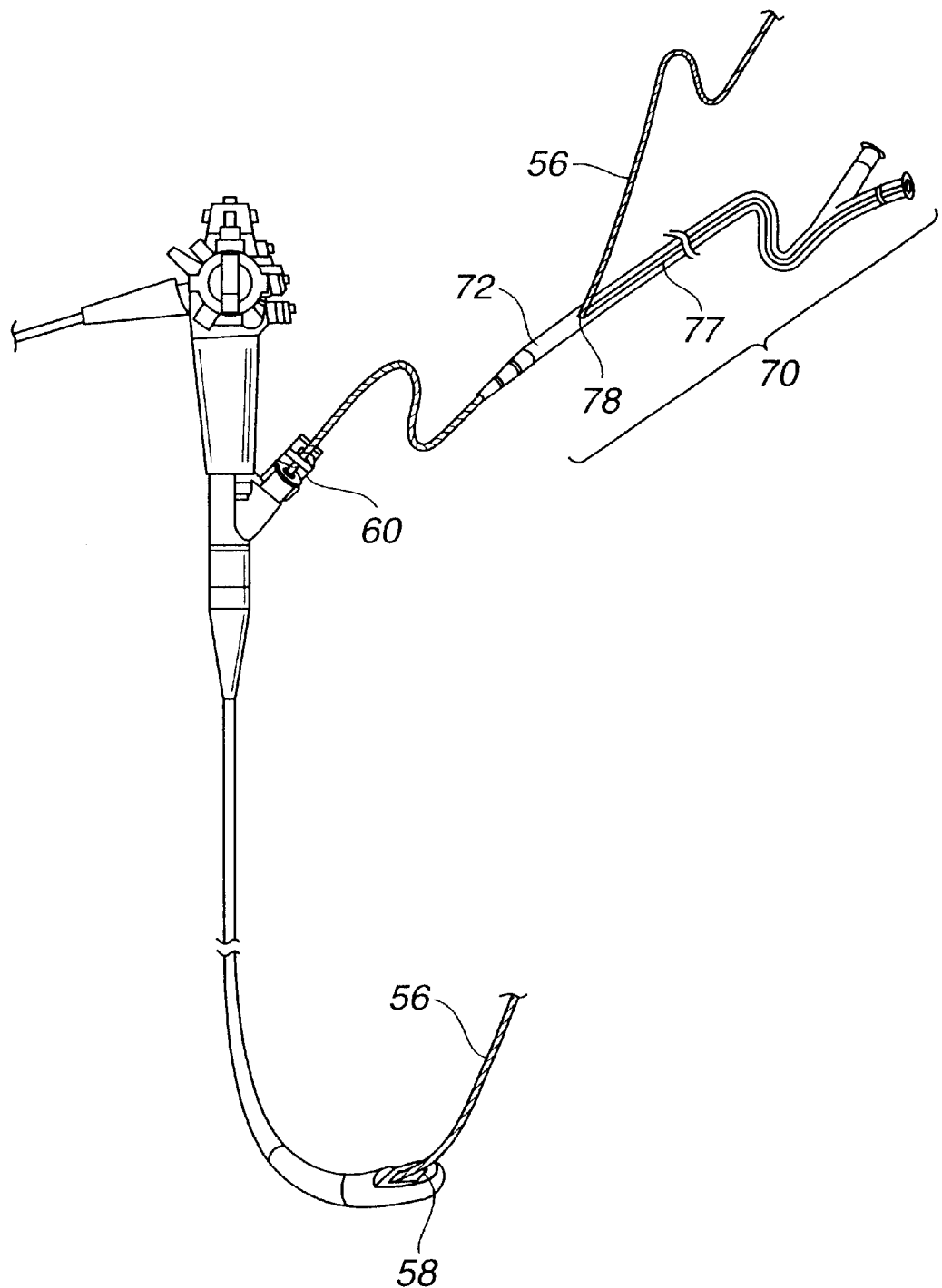
FIG. 10 is a diagram depicting the state in which the guidewire from the endoscope of the endoscope system according to the first embodiment of the present invention is pulled from the guidewire fixing treatment instrument, and the guidewire fixing treatment instrument is removed from the forceps opening of the endoscope.

FIG. 10 depicts a situation in which the guidewire 56 is pulled out of the guidewire fixing treatment instrument 70 and the guidewire fixing treatment instrument 70 is disconnected from the forceps opening 39 of the endoscope 1.

As depicted in FIG. 10, the guidewire fixing treatment instrument 70 causes the guidewire 56 to be inserted from the forceps opening 39 of the endoscope 1, such that the tip of the guidewire 56 protrudes outward from the tip 17 of the insertion portion 12. The guidewire 56 is then pulled from the guidewire fixing treatment instrument 70, and the guidewire fixing treatment instrument 70 is disconnected from the aforementioned forceps opening 39.

FIGS. 11A and 11B will next be used to describe the structure of the aforementioned guidewire fixing treatment instrument 70 using the guide catheter 71 as an example.

This guide catheter 71 is used during insertion into the mammary papilla with an orally-inserted endoscope, primarily by means of ERCP (Endoscopic Retrograde CholangioPancreatography) or the like. FIG. 11A is a perspective view of the guide catheter 71, and FIG. 11B is a cross-sectional diagram along the cutting-plane line P—P in FIG. 11A.

The guide catheter 71 runs along the entire length of the inner surface of the tube sheath 72, and is provided with a guidewire lumen 73 and contrast imaging lumen 74.

The proximal end of the tube sheath 72 is divided into a substantial Y-shape, with one side provided with a guidewire orifice 75 threaded through with the guidewire lumen 73, and the other side provided with a contrast imaging orifice 76 threaded through with the contrast imaging lumen 74.

A slit 77 is formed in part of the periphery of the guidewire lumen 73, and this slit opens in the axial direction of the tube sheath 72.

The slit edge 78 at the distal end of the slit 77 is formed in a location approximately 20 cm from the tip of the tube sheath 72. The remainder of the slit 77 extends up to the guidewire orifice 75.

When the guidewire is fixed by the first guidewire fixing means, the aforementioned slit 77 may form a distal-end slit edge as a position in contact with the distal end of a treatment instrument threaded over the guidewire, from which the remaining slit edge may extend up to the guidewire orifice 75.

The width of the slit 77 is also less than the external diameter of the guidewire 56, and is set to a width such that the guidewire 56 can be pulled towards the outside of the tube sheath 72 from the guidewire lumen 73 via the slit 77.

Furthermore, the guidewire lumen 73 may share the same lumen as the contrast imaging lumen 74 in the distal side beyond the slit edge 78 at the distal-end portion of the slit 77, and the diameter thereof may be narrowed in order to enhance threadability into the mammary papilla.

The guidewire fixing treatment instrument 70 was described in the present embodiment using the guide catheter 71. It is apparent, however, that other possible applications include treatment instruments such as a high-frequency knife having a guidewire lumen 73 with a slit 77, a balloon dilator, a pusher tube for stent insertion, and the like.

The aforementioned first guidewire fixing means was also described in the present embodiment using an example wherein the guidewire 56 is held in place between the guidewire catch groove 58 and the rigid tip 21 in the guide plane 29 of the treatment instrument elevator 27 (see FIGS. 2 and 5). However, the first guidewire fixing means used in the endoscope system of the present invention may also be configured as depicted in FIGS. 12A and 12B.

In this case, a snare 81 exposed to the outside from the posterior end surface of the slit 19 in the tip 17 via the channel inside the insertion portion 12 is disposed in the first guidewire fixing means as depicted in FIG. 12A, and the guidewire 56 is inserted in the snare 81.

Figure 12B:
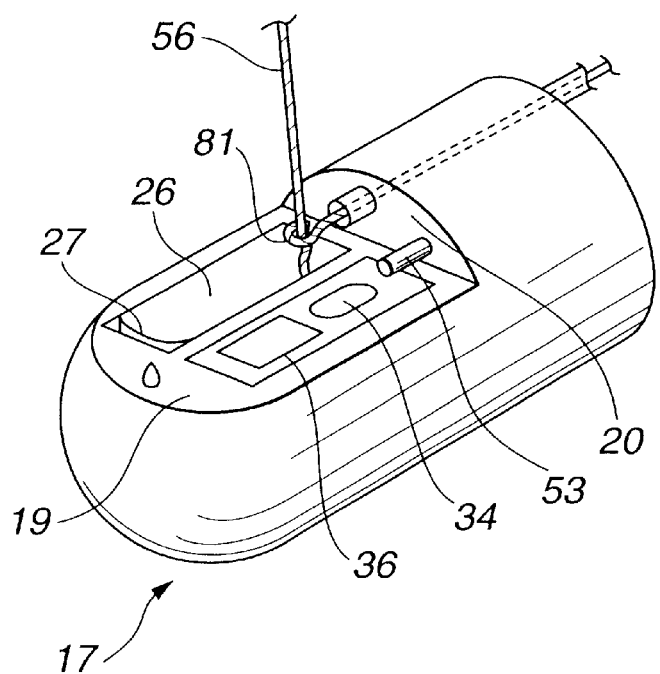
FIG. 12B is a diagram depicting the situation in which a wire connected to a snare in the state shown in FIG. 12A is pulled from the operating portion, and the guide catheter is releasably secured by the snare.

As depicted in FIG. 12B, the first guidewire fixing means is capable of catching and releasing the guide catheter 55 in the snare 81 by pulling on the wire connected to the snare 81 from the operating portion 13.

Figure 13A:
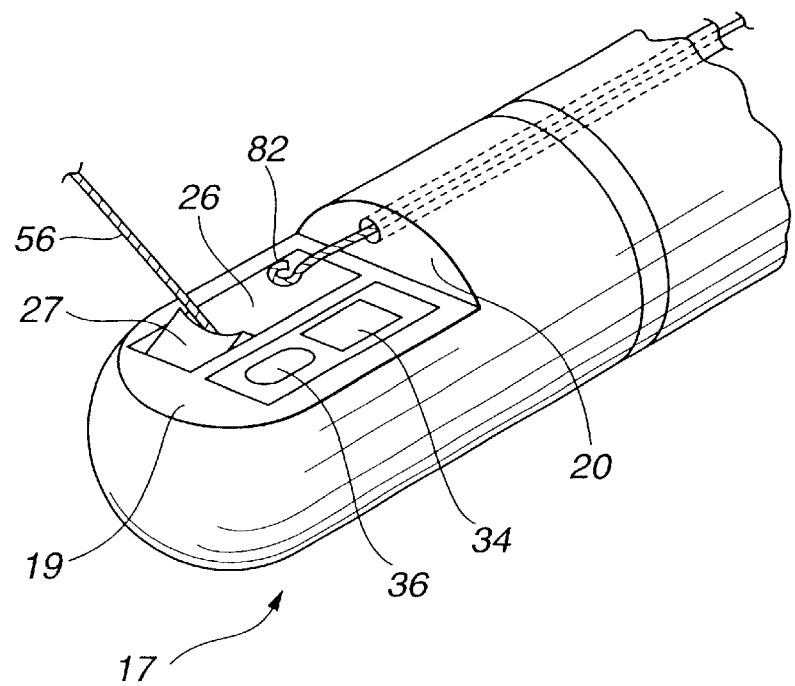
FIG. 13A is a diagram depicting the second additional embodiment of the tip of the endoscope insertion portion of the endoscope system according to the first embodiment of the present invention.
Figure 13B:
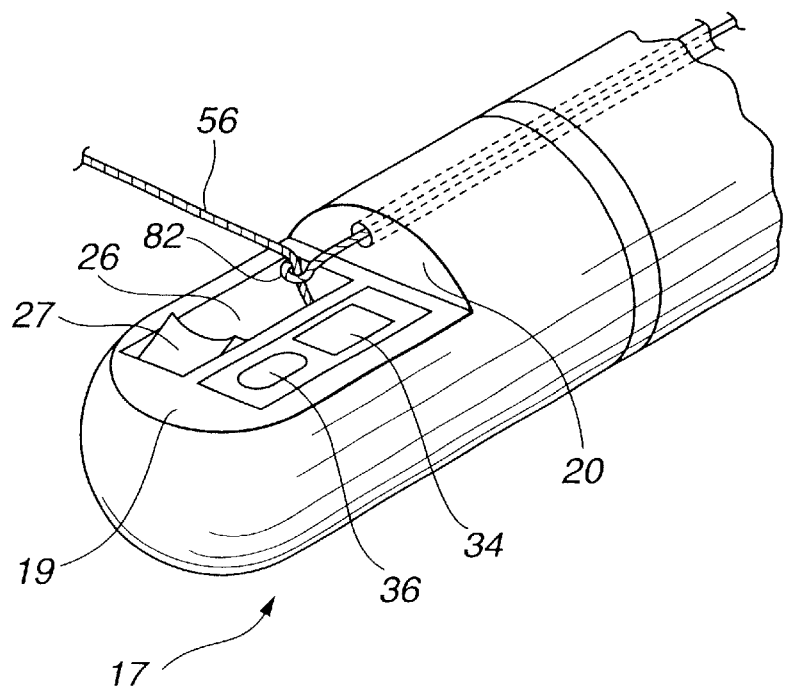
FIG. 13B is a diagram depicting the situation in which a wire connected to a hook in the state shown in FIG. 13A is pulled from the operating portion, and the guide catheter is releasably secured by the hook.

The first guidewire fixing means may also be configured as depicted in FIGS. 13A and 13B, instead of having a snare 81.

In this case, a hook 82 exposed to the outside from the posterior end surface of the slit 19 in the tip 17 via the channel inside the insertion portion 12 is disposed in the first guidewire fixing means as depicted in FIG. 13A, and the guidewire 56 is caught in the hook 82.

As depicted in FIG. 13B, the first guidewire fixing means is capable of catching and releasing the guide catheter 55 in the hook 82 by pulling on the wire connected to the hook 82 from the operating portion 13.

Figure 14A:
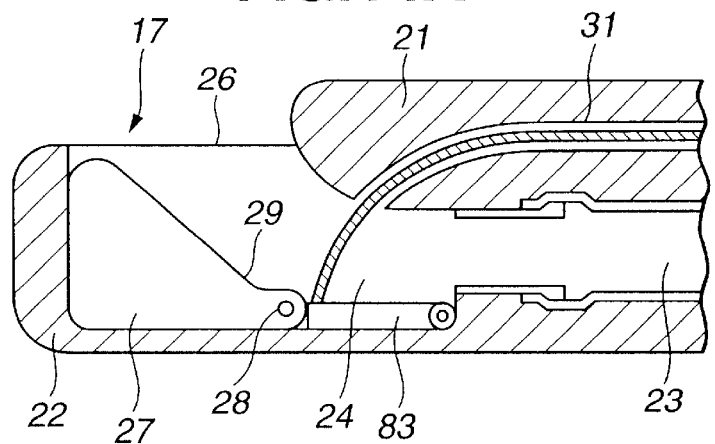
FIG. 14A is a diagram depicting the third additional embodiment of the endoscope system according to the first embodiment of the present invention.
Figure 14B:
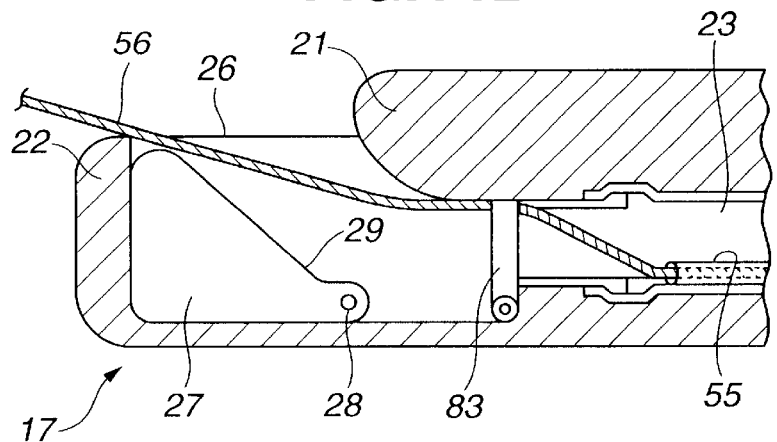
FIG. 14B is a diagram depicting the situation in which the guidewire is held tight by the rigid tip portion from the state thereof depicted in FIG. 14A.

Furthermore, the first guidewire fixing means may also be configured as depicted in FIGS. 14A and 14B.

In this case, the first guidewire fixing means can also rotate about a rotating shaft provided inside the insertion guide passage 24 at the rear of the treatment instrument elevator 27 (as depicted in FIG. 14A), and can be provided with a latching piece 83 for pinching the guidewire 56 in the space between the rigid tip 21.

The latching piece 83 can be threaded through the guide pipe 31 disposed in the insertion portion 12, and can rotate about the rotating shaft in response to manipulation of the wire connected to the distal end thereof, such that the guidewire 56 is held against the aforementioned rigid tip 21, as shown in FIG. 14B.

In the endoscope system thus configured, the guide catheter 71 is inserted into the treatment instrument threading channel 23 from the forceps opening 39 of the operating portion 13 of the endoscope 1.

Figure 7:
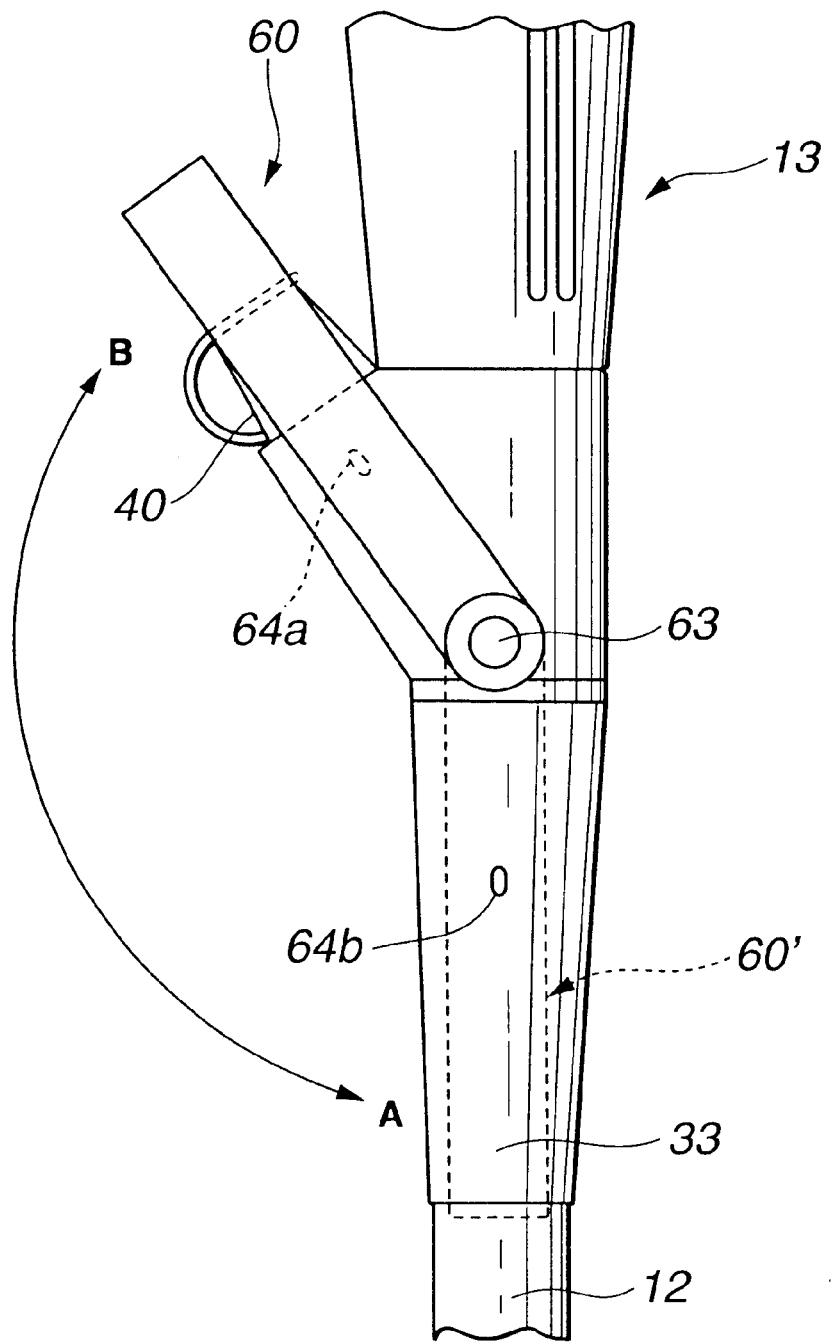
FIG. 7 is a diagram depicting the operation of the forceps opening provided to the endoscope operating portion in the endoscope system according to the first embodiment of the present invention.

The engaging prong 65 of the main body portion 61 and the catch groove 64b provided to the insertion portion protecting member 33 are then engaged and locked such that the second guidewire fixing portion 60 is disposed at position A depicted by the dotted line 60' in FIG. 7.

With the second guidewire fixing portion 60 situated at location A in the figure, the guide catheter 71 is inserted towards the treatment instrument threading channel 23 of the insertion portion 12 from the forceps opening 39 of the operating portion 13 of the endoscope 1. The guide catheter 71 then protrudes outward from the channel opening 26 of the tip 17 of the insertion portion 12, and is inserted into the pancreatic/biliary duct (not shown) in a transpapillary fashion.

The second guidewire fixing portion 60 is rotated and fixed in position B in FIG. 7 when the guide catheter 71 is inserted all the way to a prescribed location.

The guidewire 56 is then inserted from the guidewire orifice 75 of the guide catheter 71. The guidewire 56 is thus threaded through the guidewire lumen 73, and the distal portion thereof is inserted all the way to the pancreatic/biliary duct. This procedure is confirmed by radioscopy or the observation image (endoscopic image) of the endoscope 1.

When insertion of the distal portion of the guidewire 56 into the pancreatic/biliary duct is confirmed, the assistant grips the guidewire orifice 75 and the guidewire 56 extended from the guidewire orifice 75 of the guide catheter 71. The assistant then pulls in the direction of the diameter of the tube sheath 72 so as to remove the guidewire 56 from the slit 77, and pulls the guidewire 56 out of the guidewire lumen 73 to the outside.

The assistant then secures and latches the guidewire 56 in the gripping portion 62 when the guidewire 56 extracted from the guidewire lumen 73 is pulled to the location of the gripping portion 62 of the second guidewire fixing portion 60.

When fixing of the guidewire 56 in the gripping portion 62 of the second guidewire fixing portion 60 is confirmed, the operator removes the guide catheter 71 from the treatment instrument threading channel 23 of the insertion portion 12.

When the slit edge 78 of the guidewire lumen 73 has been pulled up to the location of the second guidewire fixing portion 60 by removal of the guide catheter 71, the operator manipulates the elevation operator knob 48 to pull the elevator wire 30 and rotates the treatment instrument elevator 27 about the elevator turning support 28.

As depicted in FIG. 5A, the treatment instrument elevator 27 is then raised, and the guidewire 56 is guided into the guidewire catch groove 58 along the substantially V-shaped groove formed in the guide plane 29 in conjunction with this raising, and is engaged in the guidewire catch groove 58, as shown in FIG. 5B.

By the raising of the treatment instrument elevator 27, the guidewire 56 is pushed towards the upper surface 59 of the insertion guide path of the rigid tip 21, in the direction indicated by the arrow P in FIG. 5A.

At this time, the rigid guidewire 56 tends to remain straight, a reactive force indicated by the arrow Fr in FIG. 5A acts thereon, and the guidewire is pressed into the guidewire catch groove 58 and is firmly locked in place, and is thus mechanically fixed.

When it is confirmed that the guidewire 56 has been fixed by the first guidewire fixing means with the aid of the treatment instrument elevator 27 and the rigid tip 21, the operator or assistant manually releases the fixing lock of the guidewire 56 by means of the gripping portion 62 of the second guidewire fixing portion 60, and completely removes the guide catheter 71 from the guidewire 56. At this time, an independent fixing capacity of 3 N-9.8 N (approximately 300 gf–1000 gf; where gf is grams-force) is preferable.

Specifically, the operator or assistant threads the guide catheter 71 from the forceps opening 39 of the operating portion 13 of the endoscope 1 to the channel opening 26 of the tip 17 via the treatment instrument threading channel 23 of the insertion portion 12, threads the guidewire 56 from the guidewire orifice 75 of the guide catheter 71 via the guidewire lumen 73, pulls only the guidewire lumen 73 out to the location of the first guidewire fixing means when the guidewire protrudes up to the target region, and removes the guide catheter 71 after fixing and locking the distal end of the guidewire 56 by the first guidewire fixing means provided to the tip 17.

When the guide catheter 71 is removed, the operator or assistant pulls the guidewire 56 in the radial direction of the tube sheath 72 from the guidewire lumen 73 via the slit 77 and removes the distal end of the guide catheter 71 to the outside from the forceps opening 39 of the operating portion 13, whereby the guidewire 56 is fixed and locked in relation to the gripping portion 62 of the second guidewire fixing portion 60, and the guide catheter 71 is completely removed from the proximal end of the guidewire 56.

By so doing, the operator or assistant uses the guidewire 56 threaded from the forceps opening 39 of the operating portion 13 of the endoscope 1 to the tip 17 of the insertion portion 12, inserts a guidewire fixing treatment instrument 70 of a new treatment instrument from the proximal side of the guidewire 56, and threads the guidewire fixing treatment instrument 70 of the new treatment instrument through the treatment instrument threading channel 23 by employing the guidewire 56 as a guide member.

When the distal end of the guidewire fixing treatment instrument 70 of the new treatment instrument has passed through the second guidewire fixing portion 60, the operator or assistant pulls the guidewire 56 past the slit 77 of the guidewire fixing treatment instrument 70 of the new treatment instrument and temporarily fixes/locks the guidewire with the gripping portion 62 of the second guidewire fixing portion 60.

The operator or assistant then operates the elevation operator knob 48, releases the raising of the treatment instrument elevator 27, and inserts the guidewire fixing treatment instrument 70 of the new treatment instrument to the target region.

In this manner, the operator or assistant can insert the guidewire fixing treatment instrument 70 as needed with the guidewire 56 threaded through the insertion portion 12 of the endoscope 1 acting as a guide member, by repeating the insertion procedure for the guidewire fixing treatment instrument 70 in the same way.

Specifically, there is no need for the operator and assistant to exchange treatment instruments in close quarters with one another as in conventional practice, and it is possible for an assistant, or when necessary, an operator and an assistant to exchange the treatment instrument without having to work nearby one another, because the guidewire can be fixed at both the handle and the distal end of the insertion portion of the endoscope in the endoscope system of the present embodiment.

The guidewire can be fixed, and the slit length can be reduced in the endoscope system of the present embodiment as well when fixing the guidewire by means of the first guidewire fixing means, because the distal-end slit edge is placed at a contacting location according to the selection of treatment instruments threaded over the guidewire. For this reason, the endoscope system of the present embodiment can be provided with a strong and flexible tube sheath, and insertability is enhanced.

In addition, the ease of the slit insertion process in the endoscope system of the present embodiment is connected with reduction in costs.

Furthermore, a guidewire lumen and a contrast imaging lumen are necessary in conventional practice, but because the sections containing the two lumens may be designed shorter on the handle side of the endoscope system in accordance with the present embodiment, the tube sheath diameter of the tip and insertion portion can be reduced.

(Second Embodiment)

The second embodiment of the endoscope system of the present invention will next be described using FIGS. 20 through 24.

Figure 3:
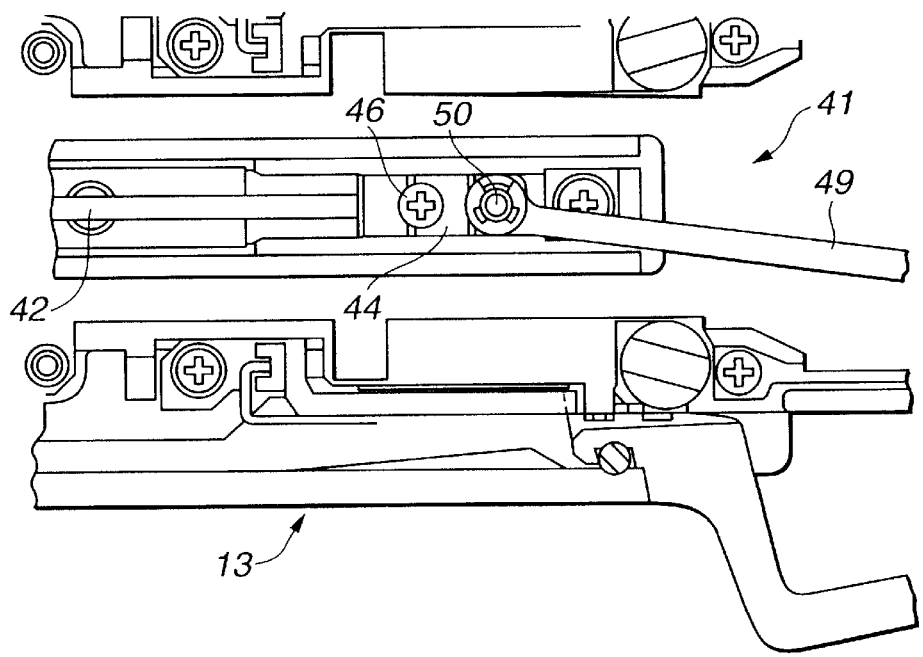
FIG. 3 is a plan view depicting the structure of the endoscope operating portion of the endoscope system according to the first embodiment of the present invention.
Figure 4:
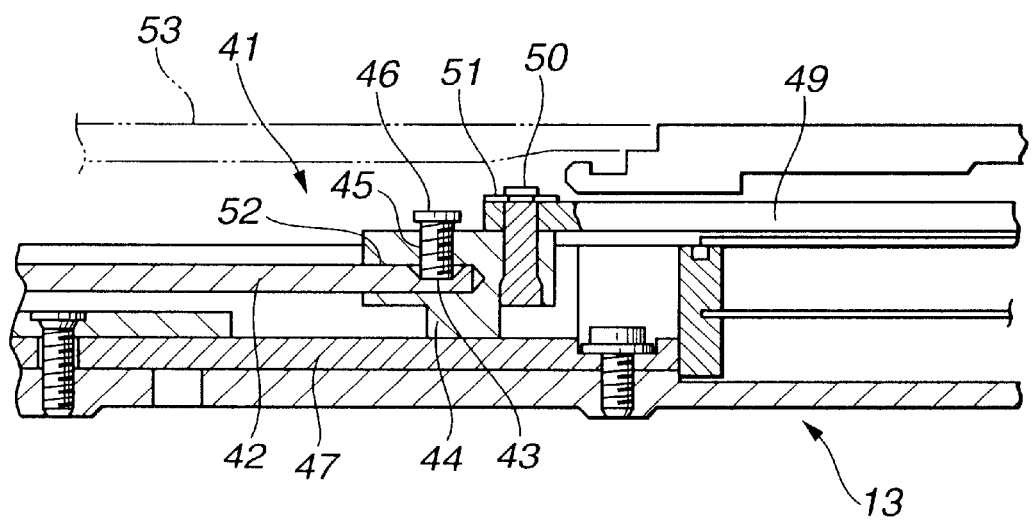
FIG. 4 is a cross-sectional view depicting the structure of the endoscope operating portion of the endoscope system according to the first embodiment of the present invention.

Identical symbols are used for the same components as in FIGS. 3 and 4, and detailed description thereof is omitted.

An elevator operating mechanism 41 designed for operating a treatment instrument elevator 27 and housed within the operating portion 13 of an endoscope 1 will first be described using FIGS. 20 and 21.

A link member 44 for fixing the proximal end of the aforementioned wire fixing member 42 is provided so as to move back and forth in the axial direction of the operating portion 13 on a horseshoe-shaped guide member 47, which is described later.

The link member 44 has a pressing extension 122 in the direction of the pull of the elevator wire 30. A pressure-receiving plate 123 is also provided at a location facing the pressing extension 122. The pressure-receiving plate 123 is brought into contact with an elastic member 124 provided inside the guide member 47.

The other end of the aforementioned elastic member 124 is held in place by a fixing extension 125 provided to the guide member 47. The elastic member 124 is positioned between the fixing extension 125 and the pressure-receiving plate 123 in a state in which some additional force has been added, rather than being at the natural length thereof.

A coil spring is used here for the elastic member 124, but a leaf spring may also be used if the same effects are achieved.

Figure 22:
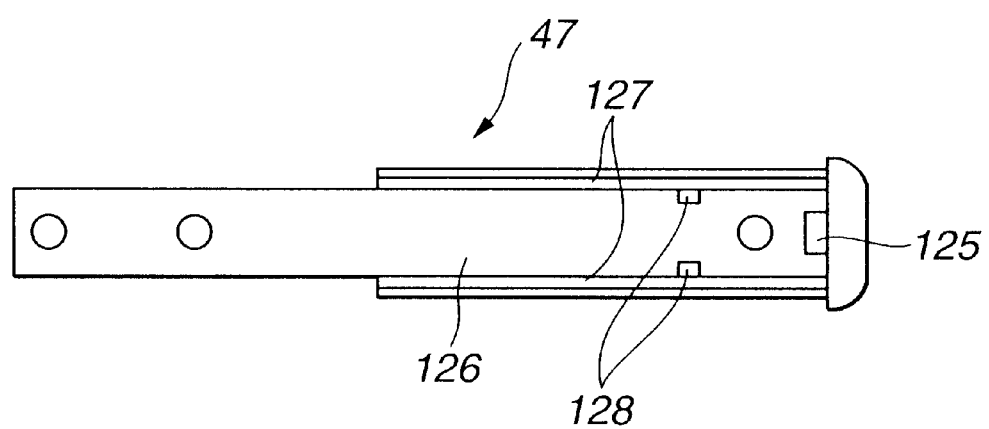
FIG. 22 is a plan view depicting the structure of the guide member of the elevator operating mechanism housed in the operating portion of the endoscope according to the second embodiment of the present invention.

The aforementioned guide member 47 will be described using FIG. 22.

The guide member 47 comprises a sliding surface 126 that corresponds to the size of the link member 44, and guide walls 127 supported by the sliding surface guide.

The guide member 47 is designed such that the link member 44 is able to slidably rest on the sliding surface 126 between the guide walls 127.

Specifically, the guide walls 127 and the sliding surface 126 act as surfaces having little friction with respect to the link member 44.

Protruding fixings 128 are formed on part of the guide walls 127. The pressure-receiving plate 123 is acted upon by the elastic member 124 and is caused to come into contact with the fixings 128 and fix the proximal end of the aforementioned elastic member 124 by means of the fixing extension 125 provided to the proximal end of the guide member 47.

The location of the fixings 128 is set such that the pressing extension 122 and pressure-receiving plate 123 of the link member 44 come into contact with each other at a location in which a warning should be issued when the treatment instrument elevator 27 is turned and raised. This warning location is defined specifically as a location at which a mini-scope, ultrasound probe, or the like could be damaged when inserted into the treatment instrument threading channel 23 and elevated.

Figure 20:
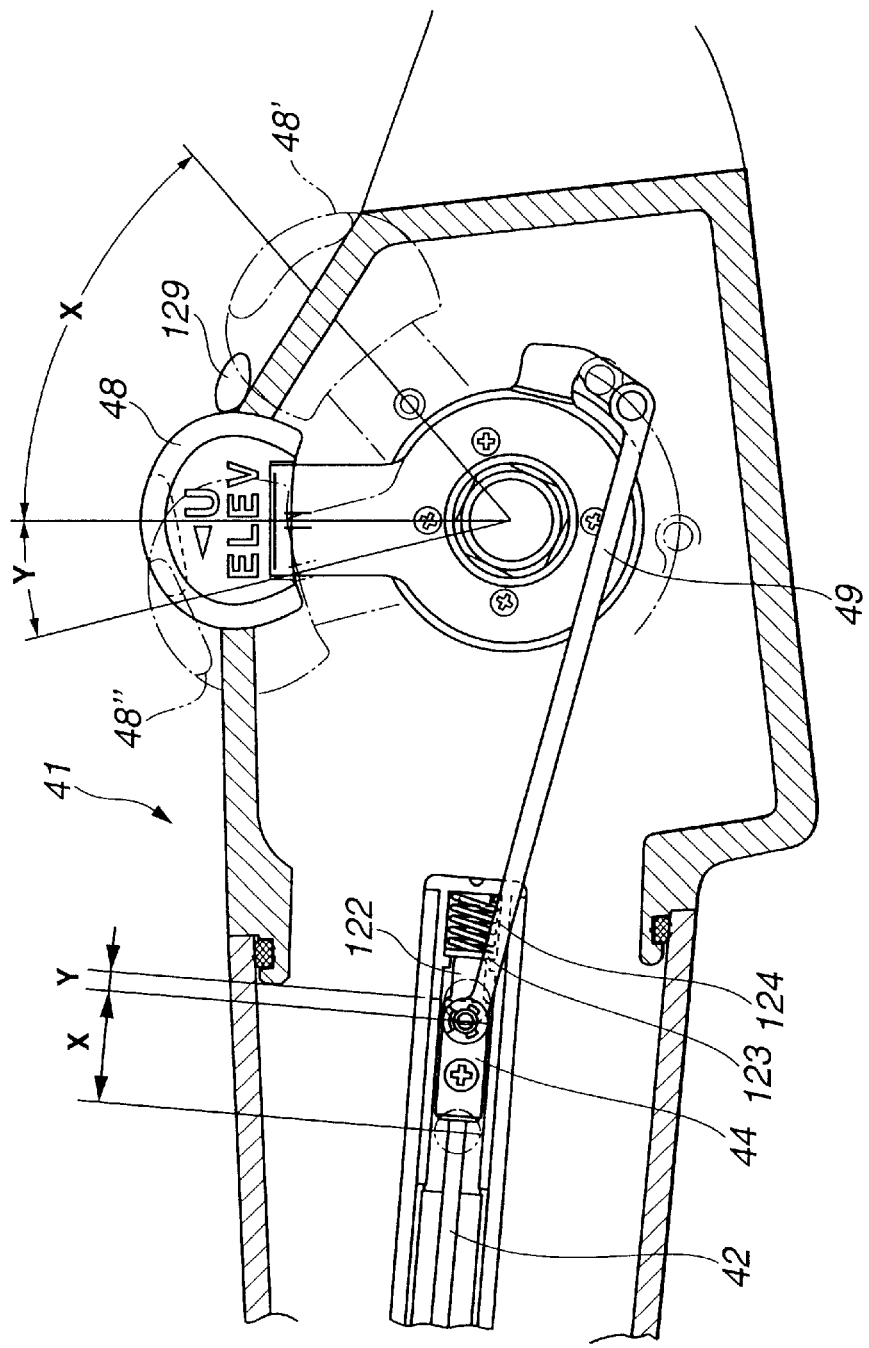
FIG. 20 is a fragmentary cross-sectional view depicting the elevator operating mechanism housed in the operating portion of the endoscope according to the second embodiment of the present invention.
Figure 21:
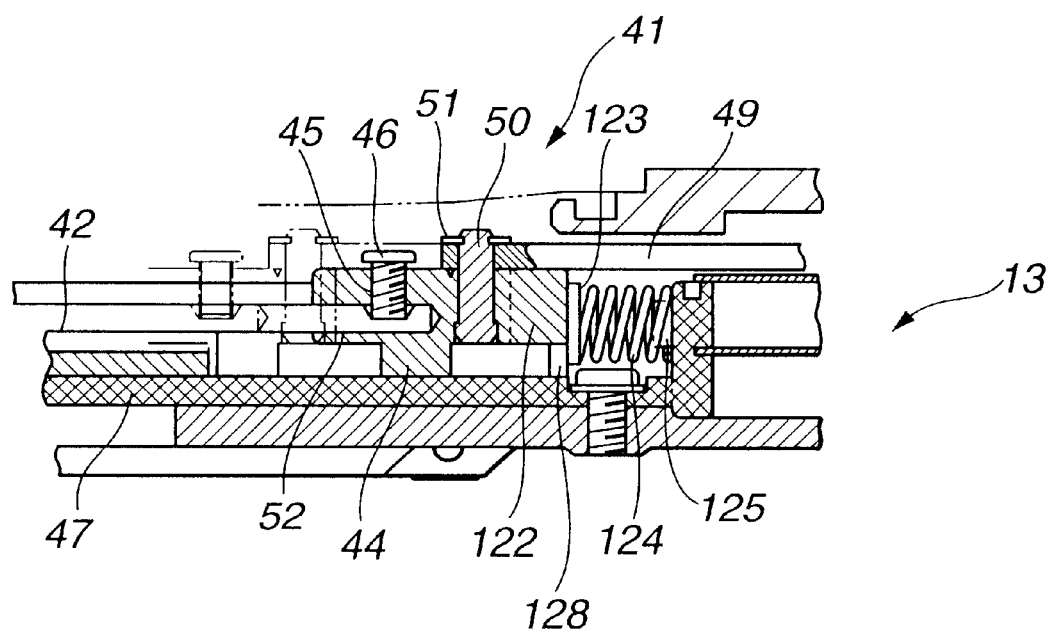
FIG. 21 is a lateral cross-sectional view depicting the detailed structure of the elevator operating mechanism housed in the operating portion of the endoscope according to the second embodiment of the present invention.
Figure 24:
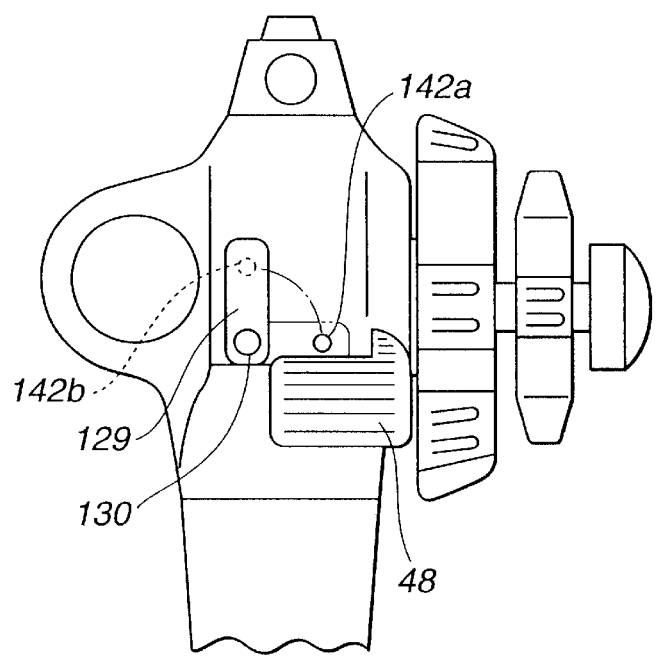
FIG. 24 is a front view depicting the elevation operator knob provided to the operating portion of the endoscope according to the second embodiment of the present invention.

The elevation operator knob 48 provided to the aforementioned operating portion 13 is provided with a knob-fixing member 129 at a location in which contact with the elevation operator knob 48 is achieved when the elevation operator knob 48 is turned all the way, as depicted in FIGS. 20 and 24.

The knob-fixing member 129 is firmly fixed to the operating portion 13 by a rotating shaft 130. A locking prong (not shown) used for positioning purposes is provided to the knob-fixing member 129 on the surface opposite the operating portion 13.

The operating portion 13 is provided with the locking grooves 142a and 142b engageable with the aforementioned locking prong. The locking groove 142a is provided-at a location for fixing the aforementioned elevation operator knob 48. In addition, the locking groove 142b is provided at a location in which the elevation operator knob 48 does not rotate.

The elevation operator knob 48 is manipulated in a rotating fashion from the position depicted by the double dotted line 48' in FIG. 20 to the position depicted by the solid line, within the first elevation range X also depicted therein. The aforementioned knob-fixing member 129 is then engaged in the locking groove 142b.

Figure 23A:
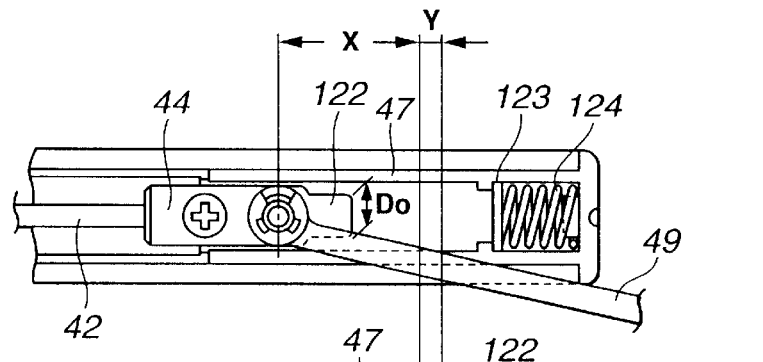
FIG. 23A is a diagram depicting the operation of the elevator operating mechanism housed in the operating portion of the endoscope according to the second embodiment of the present invention.
Figure 23B:
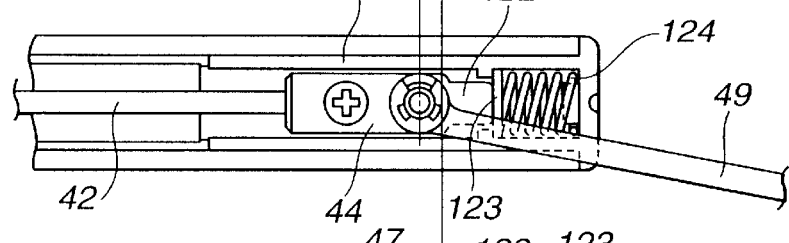
FIG. 23B is a diagram depicting the operation during the sliding movement of the ring member from the situation thereof depicted in FIG. 23A.
Figure 23C:
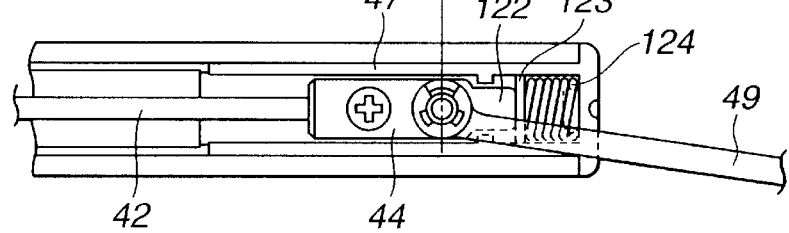
FIG. 23C is a diagram depicting the situation wherein the elevation operator knob is rotated from the situation thereof depicted in FIG. 23B, and the ring member is pulled.

The link member 44 slides from the position depicted in FIG. 23A to the position depicted in FIG. 23B when the elevation operator knob 48 is rotated within the first elevation range X, with the aforementioned locking prong engaged in the location of the locking groove 142b of the knob-fixing member 129.

In other words, the link member 44 is slid within the first elevation range X.

When the elevation operator knob 48 is rotated from the position depicted by the solid line in FIG. 20 past the first elevation range X and moved to the position indicated by the dashed line 48" in FIG. 20, the pressing extension 122 of the aforementioned link member 44 comes into contact with the pressure-receiving plate 123, tending to deform the elastic member 124.

The operator who is operating the elevation operator knob 48 at this time senses the resistance involved in deforming the elastic member 124. The operator is thus able to recognize that the elevation operator knob 48 is being rotated beyond the first elevation range X towards the second elevation range Y.

Specifically, when a thick treatment instrument, miniscope, ultrasound probe, or the like is being raised beyond the safe elevation range thereof in the endoscope system of the present embodiment, the fact that elevation is proceeding beyond the safe range can be sensed bodily, and such elevation can thus be promptly terminated.

The operator also rotates the elevation operator knob 48 such that the pressing extension 122 of the link member 44 deforms the elastic member 124 via the pressure-receiving plate 123 when a usual treatment instrument or the like is elevated all the way to the second elevation range Y, which is the maximum elevation point. The elastic member 124 may then deform and pull the link member 44 to the position depicted in FIG. 23C.

Furthermore, the operator rotates and fixes the knob-fixing member 129 in the locking groove 142a when maintaining the state of maximum elevation in the second elevation range Y. In this manner, the elevation operator knob 48 and the knob-fixing member 129 can be brought into contact with each other, and the elevation operator knob 48 can be fixed.

When the fully elevated state is released, fixing of the elevation operator knob 48 can be released by the operator returning the knob-fixing member 129 to the original position thereof in the locking groove 142b.

In this manner, the endoscope system of the present embodiment can issue a warning to the operator when a certain elevation range has been exceeded, by means of a load being placed on the elevation operator knob 48 when the elevation operator knob 48 is rotated. Costly and fragile treatment instruments such as mini-scopes and the like can thus be used safely in the endoscope system of the present embodiment, even when the elevation angle is improperly increased by mistake.

The need for brushing or otherwise treating the portions of complex warning means is also eliminated, because the warning member is provided within the operating portion of the endoscope system of the present embodiment. The endoscope system of the present embodiment can therefore be washed, sterilized, or otherwise treated in the conventional manner.

The same effects are obtained using an endoscope in which the elevation angle for fixing the heretofore described guidewire is increased, and the same effects are also obtained for any endoscope having a treatment instrument elevator.

(Third Embodiment)

Figure 25:
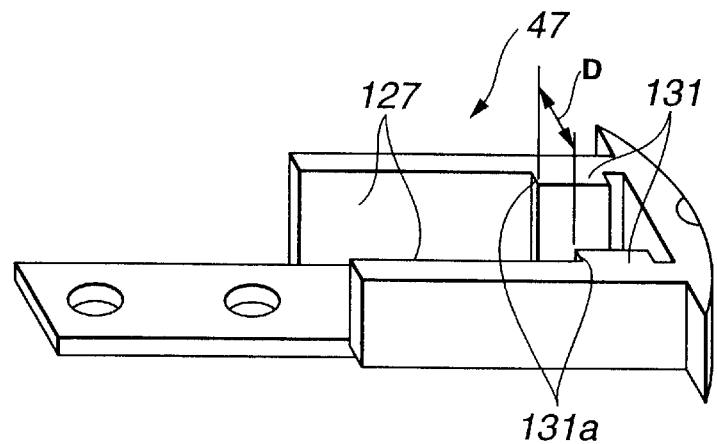
FIG. 25 is a perspective view depicting the guide member used in the elevator operating mechanism provided to the operating portion of the endoscope system according to the third embodiment of the present invention.

The third embodiment of the endoscope system of the present invention will next be described using FIG. 25. As depicted in FIG. 25, the endoscope system according to the third embodiment is provided with extensions 131 in the guide walls 127 of the guide member 47 instead of the elastic member 124 being provided to the guide member 47 for imparting a resistive load to the link member 44 when the link member 44 is slid past the first elevation range X by the rotation of the elevation operator knob 48 housed within the operating portion 13.

The width D of the space between the extensions 131 provided to the guide walls 127 is slightly greater than the with Do (see FIG. 23A) of the pressing extension 122 of the link member 44.

Specifically, the pressing extension 122 in the link member 44 is pulled and brought into contact with the extensions 131 of the guide member 47 by the rotation of the elevation operator knob 48.

The pressing extension 122 of the link member 44 enters the space between the extensions 131 of the guide member 47 because of chamfers 131a disposed on the extensions 131.

Specifically, the pressing extension 122 comes into contact with the extensions 131 and slides through the space between the extensions 131, and the pressing extension 122 then enters the space between the extensions 131 because the width Do of the pressing extension 122 of the link member 44 is slightly greater than the width D between the extensions 131 of the guide member 47.

The endoscope system of the third embodiment thus enables the operator to easily recognize when the safe range for elevation has been exceeded based on the resistance experienced when contact is established between the pressing extension 122 and the extensions 131 in the second elevation range Y, which is different from the aforementioned first elevation range X.

The guide member 47 is formed from an elastic resin such as polyester or the like.

As a result, the same effects are obtained in the endoscope system of the third embodiment as in the second embodiment of the present invention, by means of the simple provision of chamfers 131a and 131b to the guide walls 127 and 127 of the guide member 47.

The first modification of the guide member 47 of the previously described third embodiment of the present invention will next be described using FIGS. 26A and 26B.

Figure 26A:
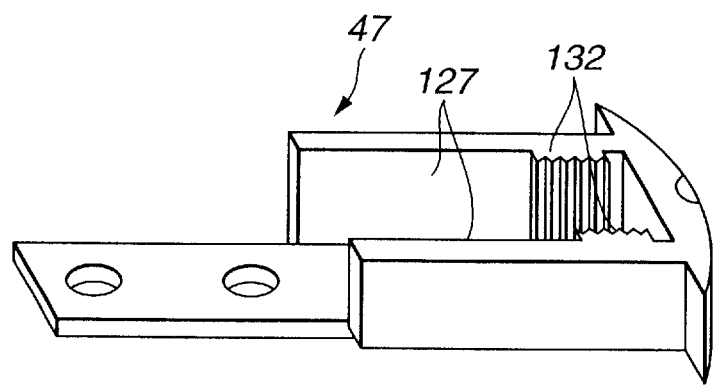
FIG. 26A is a diagram depicting the first modification of the guide member in the third embodiment of the present invention.

The first modification is provided with toothed surfaces 132 and 132 formed in a toothed shape on the mutually opposing surfaces of the guide walls 127 and 127 of the guide member 47 as depicted in FIG. 26A, instead of the chamfers 131a and 131b on the guide member 47.

Figure 26B:
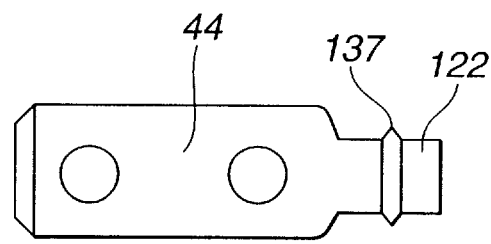
FIG. 26B is a diagram depicting the ring member provided with a prong capable of engaging with the toothed surface of the pressing extension.

In addition, the pressing extension 122 of the link member 44 is provided with a prong 137 capable of engaging with the aforementioned toothed surfaces 132, as depicted in FIG. 26B.

Specifically, the prong 137 of the link member 44 engages with the toothed surfaces 132 of the guide member 47 when the elevation operator knob 48 is elevated to the second elevation range Y beyond the first elevation range X. The sensation of the prong 137 engaging with the toothed surfaces 132 of the link member 44 is therefore conveyed to the operator. The operator is thus able to recognize when the safe elevation range has been exceeded for a mini-scope or the like.

It is also possible for an operator performing maximum elevation (second elevation range Y) with the aid of a usual treatment instrument or the like to elevate the link member 44 to the maximum elevation while remaining aware of engagement interference between the toothed surfaces 132 and the prong 137 by manipulating the elevation operator knob 48.

As a result, the warning becomes even more pronounced in the first modification because the operator continuously senses the presence of an impediment while elevating the elevation operator knob 48.

In the first modification, the elevation operator knob 48 can also be fixed in the position of the elevation range Y by the high engagement resistance between the toothed surfaces 132 of the guide member 47 and the prong 137 of the link member 44.

A second modification of the guide member 47 of the previously described third embodiment of the present invention will next be described using FIGS. 27A and 27B.

The second modification is provided with a function for issuing a warning to the operator when the elevation operator knob 48 of the operating portion 13 is rotated to the second elevation range Y passing the first elevation range X.

Figure 27A:
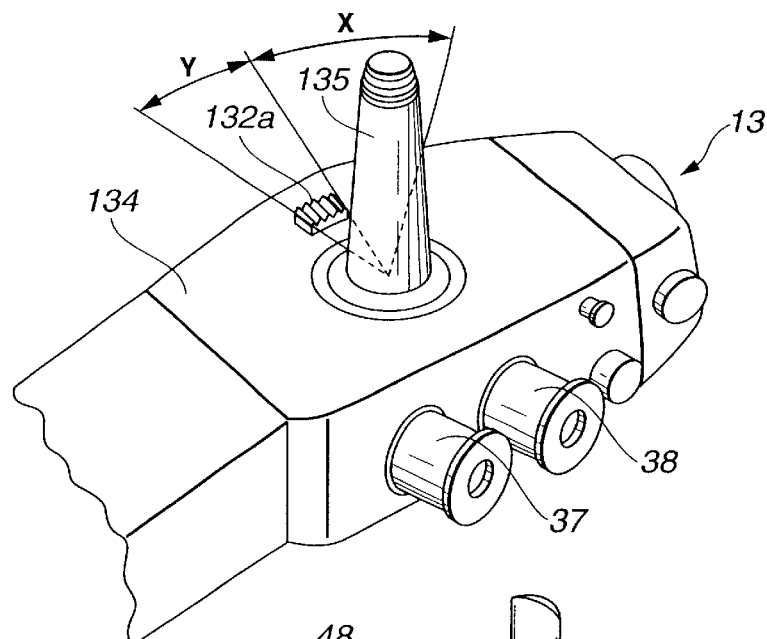
FIG. 27A is a diagram depicting the second modification of the guide member in the third embodiment of the present invention.
Figure 27B:
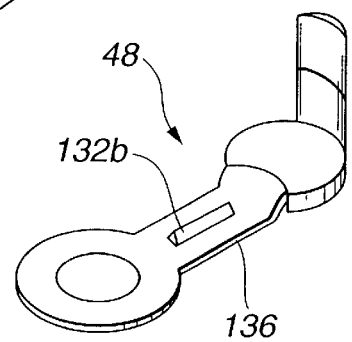
FIG. 27B is a perspective view of the rear surface of the elevation operator knob in FIG. 27A.

FIG. 27A is a diagram depicting a view wherein part of the bending operator portion 35 of the operating portion 13 is removed; and FIG. 27B is a perspective view of the rear surface of the elevation operator knob 48.

As depicted in FIG. 27A, a fixed-shaft member 135 for supporting the bending operator portion 35 and elevation operator knob 48 extends from the operator knob-side surface 134 of the operating portion 13, with the flexing operator knob of the bending operator portion 35 and elevation operator knob 48 removed from the operating portion 13. Furthermore, a toothed surface 132a is provided to the operator knob-side surface 134 surrounding the fixed-shaft member 135.

As depicted in FIG. 27B, a prong 132b is provided to the side of the arm portion 136 that comes into contact with the operator knob-side surface 134, and this portion is supported by the fixed-shaft member 135 in the elevation operator knob 48 supported by the fixed-shaft member 135.

Specifically, the prong 132b of the arm portion 136 of the elevation operator knob 48 comes into contact with the toothed surface 132a provided to the operator knob-side surface 134, such that the operator clearly senses the presence of an impediment when the elevation operator knob 48 is turned in accordance with the second modification.

The location of the toothed surface 132a is set such that the toothed surface 132a comes in contact with the prong 132b when the elevation operator knob 48 is rotated until the connected treatment instrument elevator 27 enters the warning range, or second elevation range Y, as depicted in FIG. 20.

As a result, the warning becomes even more pronounced in the second modification because the operator continuously senses the presence of an impediment while elevating the elevation operator knob 48.

The operator is also able to elevate the treatment instrument elevator 27 to the maximum elevation position while the toothed surfaces 132 engage with the prong 137 in response to the rotation of the elevation operator knob 48 when the device is elevated to the second elevation range Y, or maximum elevation, with the aid of a usual treatment instrument or the like.

(Fourth Embodiment)

The endoscope system according to the fourth embodiment of the present invention will next be described using FIGS. 28 through 30.

Figure 28:
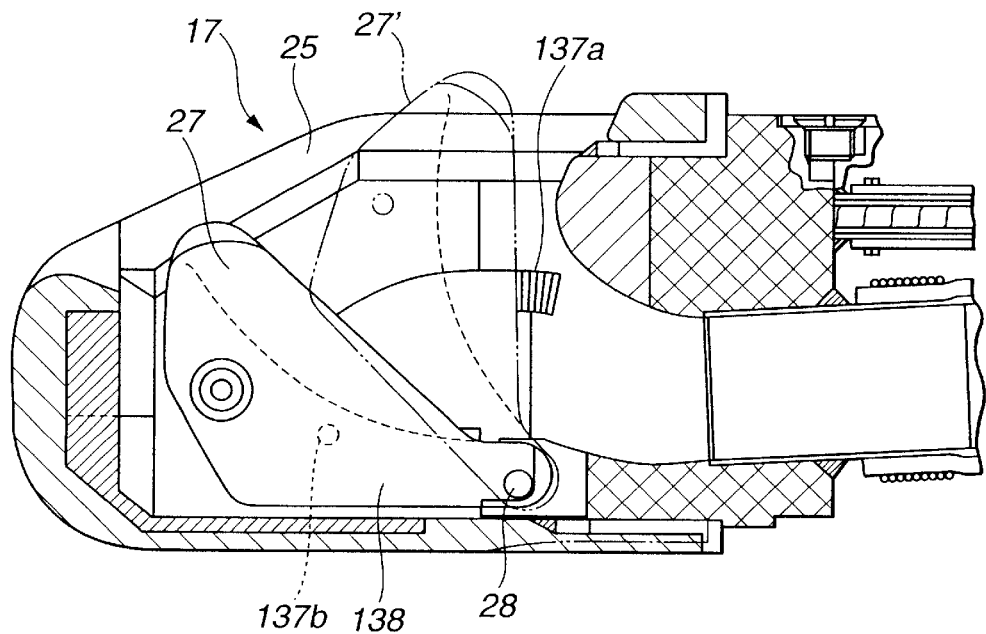
FIG. 28 is a cross-sectional diagram depicting the structure of the tip of the endoscope system according to the fourth embodiment of the present invention.
Figure 29:
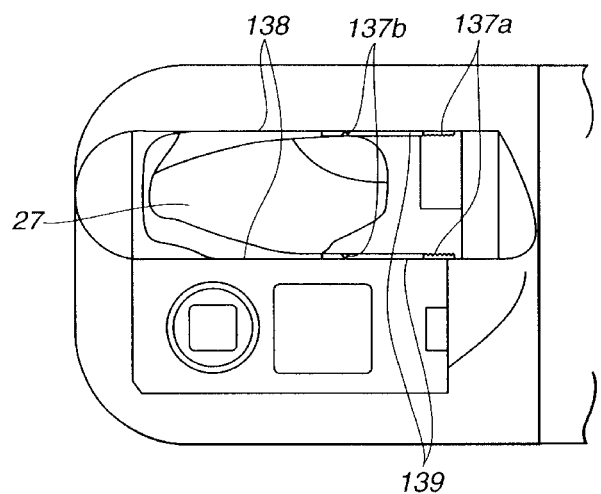
FIG. 29 is a plan view depicting the structure of the tip of the endoscope system according to the fourth embodiment of the present invention.

The endoscope system of the fourth embodiment is provided with a toothed surface 137a on the wall surface 139 of a storage chamber 25 facing the lateral surface 138 of the treatment instrument elevator 27 provided at the tip 17 of the operating portion 13, as depicted in FIGS. 28 and 29. The toothed surface 137a is provided on the periphery around the elevator turning support 28. The treatment instrument elevator 27 is also provided with a prong 137b.

The toothed surface 137a may be disposed on the treatment instrument elevator 27, and the prong 137b may be disposed on the wall surface 139. The toothed surface 137a and prong 137b may also be disposed only on one side of the lateral surface 138 and wall surface 139.

In this arrangement, when the treatment instrument elevator 27 is elevated past the first elevation range X to the second elevation range Y, the prong 137b provided to the treatment instrument elevator 27 comes into contact with the toothed surface 137a, so the operator can sense the presence of a hindrance and recognize the fact that the safe elevation range for a mini-scope or the like has been exceeded by using the endoscope system of the fourth embodiment.

The treatment instrument elevator 27 can also be elevated to the maximum elevation position while the toothed surface 137a engages with the prong 137b in response to the operation of the elevation operator knob 48 when maximum elevation (second elevation range Y) is achieved by employing a usual treatment instrument or the like.

As a result, the endoscope system of the fourth embodiment is capable of issuing a warning whereby the position in which the distal end remains consistently stable, and variations in the bridging length of the operating wire due to differences in travel (which occur because the insertion portion 12 changes its condition from straight to curved when traveling inside) are prevented from having any effect because a warning means is provided by the toothed surface 137a and prong 137b in the endoscope tip 17.

Figure 30:
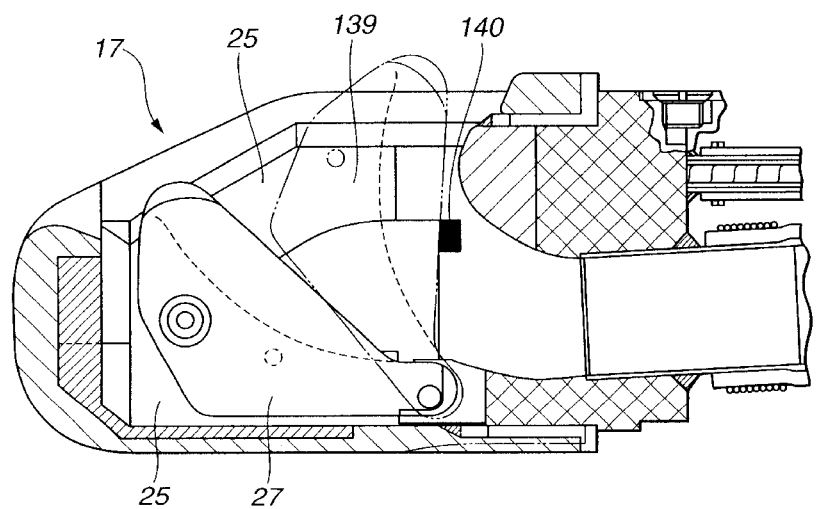
FIG. 30 is a cross-sectional view depicting a modification of the tip of the endoscope system according to the fourth embodiment of the present invention.

An elastic member 140 may also be provided instead of the toothed surface 137a of the endoscope tip 17 to the endoscope system of the fourth embodiment in a location on the wall surface 139 of the storage chamber 25 as depicted in FIG. 30, so as to provide contact with the treatment instrument elevator 27 when the treatment instrument elevator 27 is elevated to the elevation range Y warning range.

As a result, a resistive force is conveyed to the operator because of the treatment instrument elevator 27 touching the elastic member 140 when the treatment instrument elevator 27 is elevated to the warning range (second elevation range Y) in the endoscope system of the fourth embodiment. The operator can thus recognize that the safe elevation range for a mini-scope or the like has been exceeded.

The operator can also perform elevation to the maximum elevation position when performing maximum elevation (second elevation range Y) by employing a usual treatment instrument or the like, because the elastic member 140 is pushed by the treatment instrument elevator 27 and subjected to elastic deformation as a result of operating the elevation operator knob 48.

Visual means featuring a warning lamp or warning display on the monitor 4, or audible means featuring a buzzer or the like may be substituted for the tactile warning means provided to the operator in embodiments 3 through 5.

It is also apparent that graduated marks recognizable by the operator may be formed at the location of the elevation operator knob 48 to mark the transition from the first elevation range X to the second elevation range Y of the operating portion 13 for the endoscope system of the fourth embodiment.

(Fifth Embodiment)

The fifth embodiment of the endoscope system of the present invention will next be described using FIGS. 15 through 19.

The fifth embodiment relates to the structure of the first guidewire fixing means provided to the tip of the insertion portion of the previously described endoscope system.

Figure 15:
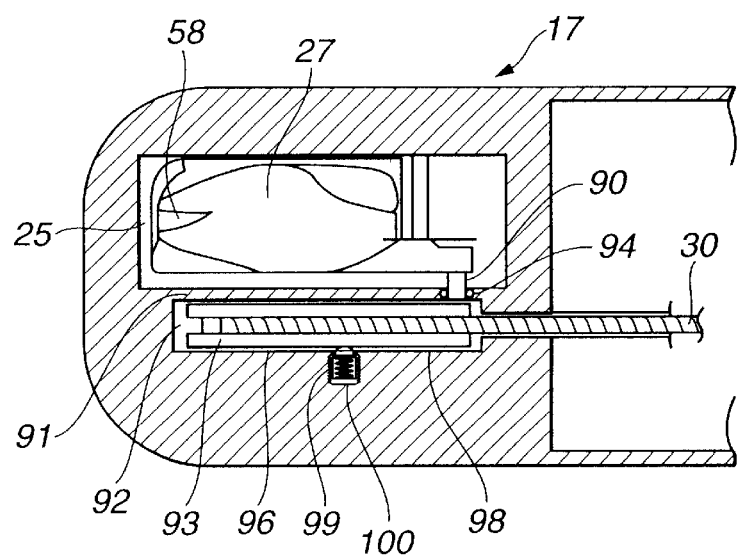
FIG. 15 is a plan view of the tip of the endoscope insertion portion of the endoscope system according to the fifth embodiment of the present invention.

The structure of the tip 17 of the fifth embodiment will first be described using FIGS. 15 and 16.

The tip 17 of the aforementioned insertion portion is provided with a storage chamber 25 disposed within the treatment instrument elevator 27. This treatment instrument elevator 27 has the aforementioned guide plane 29. A guidewire catch groove 58 for releasably securing solely the guidewire 56 is provided to the apex portion of the guide plane 29.

The treatment instrument elevator 27 is rotatably fixed to the side wall 91 of the storage chamber 25 by a fixed-shaft member 90. An airtight space 92 disposed parallel with the storage chamber 25 extends to one end of the fixed-shaft member 90.

One end of an arm 93 is fixed by the fixed-shaft member 90 extending into the airtight space 92. The other end of the arm 93 is connected to the elevator wire 30 threaded inside the airtight space 92, and the component is connected with an elevator operating mechanism 41 provided to the operating portion 13.

The arm 93 and the treatment instrument elevator 27 are rotated as a single body by means of the operation of the elevation operator knob 48.

The airtight space 92 is kept airtight by placing an O-ring 94 between the fixed-shaft member 90 and the side wall 91 along the storage chamber 25.

The detailed structure of the arm 93 disposed in the airtight space 92 will next be described using FIGS. 16 and 17.

An arcuate engagement groove 96 is formed in the side surface 95 of the arm 93 about the fixed-shaft member 90. A pressure surface 97 is formed at the tip of the arcuate engagement groove 96. The pressure surface 97 and the side surface 95 lie within the same surface, and are in a position one level higher than the arcuate engagement groove 96. A female screw hole 99 is also formed in the wall surface 98 of the airtight space 92 opposite the arcuate engagement groove 96. A temporary locking member 100 is fixed in the female screw hole 99. The locations of the female screw hole 99 and temporary locking member 100 are set such that the treatment instrument elevator 27 on the same axis as the arm 93 can be elevated two levels to allow the temporary locking member 100 to slide into and engage with the arcuate engagement groove 96 provided to the arm 93 when the treatment instrument elevator 27 is rotated to the maximum position in the elevation range of the first level.

Furthermore, when the arm 93 is rotated, the temporary locking member 100 slides towards the pressure surface 97 from the arcuate engagement groove 96 of the arm 93, reaching the second level of the elevation range of the treatment instrument elevator 27.

Figure 18:
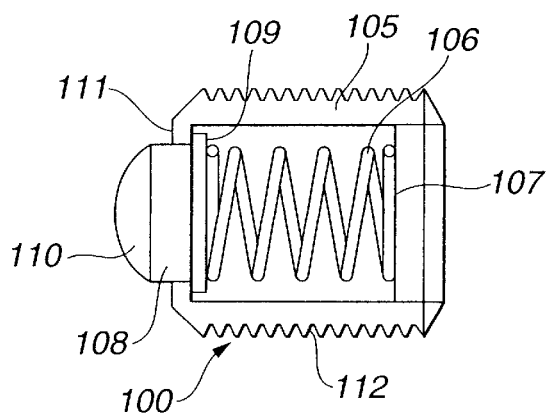
FIG. 18 is a cross-sectional view depicting the structure of the temporary locking member used in the tip of the endoscope insertion portion of the endoscope system according to the fifth embodiment of the present invention.

As depicted in FIG. 18, the temporary locking member 100 is provided with an elastic member 106 in the hollow portion of a hollow cylindrical main body 105 having a bottom. One end of the elastic member 106 comes into contact with a pressure-receiving surface 107 in the bottomed portion of the main body 105, and the other end comes into contact with an engaging member 108 provided to the opening of the hollow portion.

The engaging member 108 has a substantially hemispherical engaging portion 110 on the other side of the engaging member 108 and contacting surface 109, which contact with the elastic member 106.

The engaging member 108 comes into contact with a fixing surface 111 provided to the hollow opening portion of the main body 105, and force is constantly applied thereon from the elastic member 106 in the direction of the engaging portion 110.

A male screw 112 is also formed in the outside surface of the main body 105. The temporary locking member 100 thus configured is screwed into the female screw hole 99.

Figure 19:
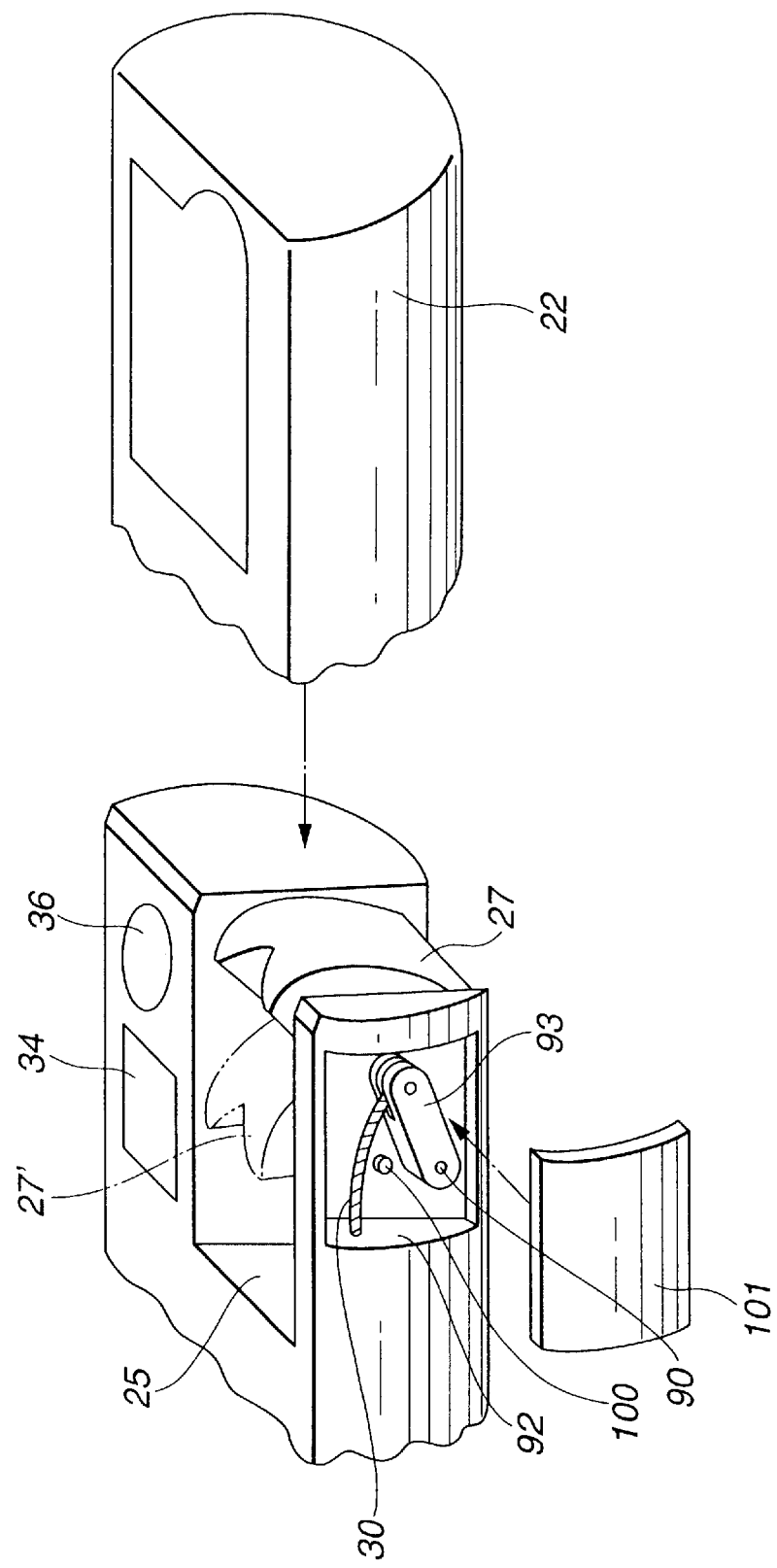
FIG. 19 is an exploded perspective view depicting a modification of the tip of the endoscope insertion portion of the endoscope system according to the fifth embodiment of the present invention.

The airtight space 92 extends through the tip 17 in parallel fashion in relation to the storage chamber 25. A substantially U-shaped groove 25' for forming the storage chamber 25 is provided to the distal substrate comprising the tip 17 as depicted in FIG. 19, and the treatment instrument elevator 27 is disposed in the U-shaped groove 25'. A concave portion for use by the airtight chamber 92' is also formed on the outer surface of the U-shaped groove 25', and the arm 93 is disposed in the airtight chamber 92'.

The arm 93 disposed in the airtight chamber 92', and the treatment instrument elevator 27 disposed in the U-shaped groove 25' are both connectedly fixed by the fixed-shaft member 90, and the temporary locking member 100 and elevator wire 30 are provided thereto.

A cover 101 is mounted over the opening of the airtight chamber 92', and airtightness is thus preserved. Furthermore, the tip 17 can be covered with a tip cover 22 everywhere except the airtight chamber 92' provided with the cover 101, and the treatment instrument elevator 27 in the U-shaped groove 25' on the side of the guidewire groove 58.

The treatment instrument elevator 27 is disposed in the storage chamber 25, the arm 93 is disposed within the airtight space 92 fixed by the fixed-shaft member 90 coaxially with the treatment instrument elevator 27, and the arcuate engagement groove 96 for engaging with the temporary locking member 100 is formed in the tip 17.

Figure 16:
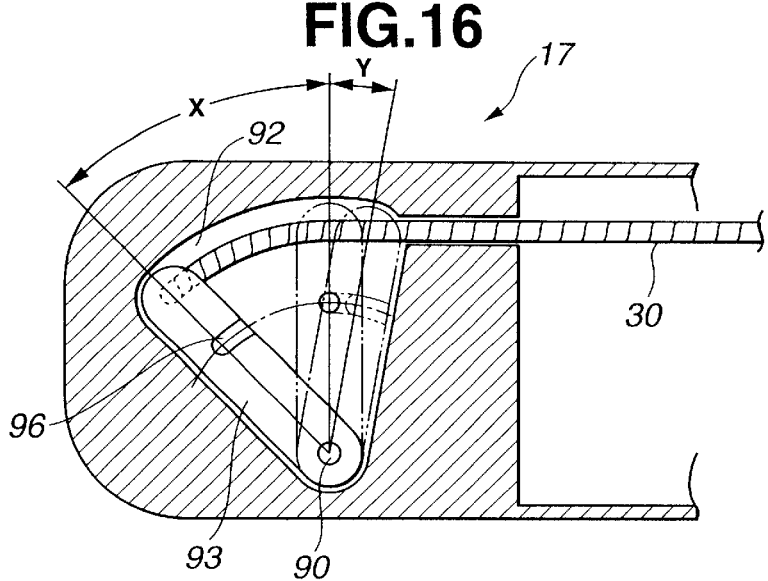
FIG. 16 is a cross-sectional diagram of the tip of the endoscope insertion portion of the endoscope system according to the fifth embodiment of the present invention.
Figure 17:
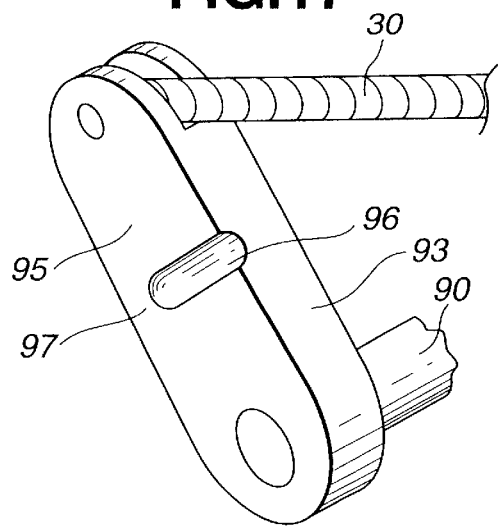
FIG. 17 is a perspective view depicting the form of the arm used for the tip of the endoscope insertion portion of the endoscope system according to the fifth embodiment of the present invention.

When the arm 93 is rotated about the fixed-shaft member 90 by the pulling of the elevator wire 30, engagement with the arcuate engagement groove 96 is achieved, whereby the temporary locking member 100 is elevated within the range indicated by X in FIG. 16 until coming into contact with the pressure surface 97, and the treatment instrument elevator 27 is elevated within the same range.

The engaging portion 110 of the temporary locking member 100 moves past the arcuate engagement groove 96, travels towards the pressure surface 97, and elevates within the Y-range shown in FIG. 16 in opposition to the force of the elastic member 106 when the arm 93 applies, by means of the elevator wire 30, a pulling force whereby the temporary locking member 100 moves past the pressure surface 97 of the arcuate engagement groove 96.

Specifically, the arm 93 is capable of elevation in the first elevation range X in which the temporary locking member 100 comes into contact with the pressure surface 97, and in the second elevation range Y in which the temporary locking member 100 moves past the arcuate engagement groove 96 and is pressed upward against the pressure surface 97 by the engagement of the arcuate engagement groove 96 with the temporary locking member 100.

The guidewire 56 alone can be firmly secured as depicted in FIG. 5 once the treatment instrument elevator 27 is maximally elevated to the second elevation range Y when the guidewire 56 threaded via the treatment instrument threading channel 23 is left inside a body cavity in the endoscope system of the fifth embodiment by using the elevating mechanism thus configured.

With the tip 17, the elevation angle may be accidentally maximized when a thick treatment instrument, mini-scope, ultrasound probe, or the like is inserted and continuously elevated past the safe elevation range with the aid of the guidewire 56.

In view of this, the aforementioned mini-scope or the like is raised such that the range extending to the maximum safe elevation angle thereof (up to the conventional maximum elevation angle) lies within the first elevation range X in the endoscope system of the fifth embodiment.

When the device is elevated past this first elevation range X, the temporary locking member 100 comes into contact with the arcuate engagement groove 96 of the arm 93 on the side of the pressure surface 97, and the force is converted to elevation force. The operator is thereby able to recognize that the first elevation range X has been exceeded.

Specifically, the treatment instrument elevator 27 is rotated and elevated up to the first elevation range X by means of the elevator operating mechanism 41 in response to the manipulation of the elevation operator knob 48 in the endoscope system of the fifth embodiment.

In this process, the temporary locking member 100 remains within the range of the engagement groove 96, and the device can be elevated in regular manner due to the lack of resistance between the arm 93 and the temporary locking member 100.

Furthermore, when the elevation angle is increased, the engagement groove 96 is engaged with the temporary locking member 100, and the fixing action of the first elevation range X takes effect.

The operator elevates the treatment instrument elevator 27 in relation to the aforementioned thick treatment instrument, mini-scope, ultrasound probe, or the like within the first elevation range X.

To exchange a treatment instrument by employing the guidewire 56 as a guide, the operator manipulates the elevation operator knob 48 in the direction of a further increase in the elevation angle in a state in which the arcuate engagement groove 96 and the temporary locking member 100 are in engagement with each other when the tip of the guidewire 56 must be locked.

When this happens, the elastic member 106 provided to the temporary locking member 100 undergoes elastic deformation, the engaging member 108 crosses over the arcuate engagement groove 96 while being pushed inside the main body 105 from the arcuate engagement groove 96 to the pressure surface 97, and the pressure surface 97 and the engaging member 108 come into contact with each other, allowing the elevation angle of the arm 93 to be further increased. The arm 93 comes into contact with the fixing portion provided to the airtight space 92, whereby the maximum angle in the second elevation range is achieved.

The operator can perform inversion such that the elevator wire 30 pushes out the arm 93, and the engaging member 108 is again held within the arcuate engagement groove 96 by manipulating the elevation operator knob 48 to invert the treatment instrument elevator 27.

The operator can selectively manipulate two elevation ranges by repeating such operations.

The endoscope system of the fifth embodiment is not limited to endoscopes for guidewire fixing and may also be used to prevent the maximum elevation angle from being abruptly established by mistake during elevation of a thick treatment instrument, mini-scope, ultrasound probe, or the like in a common endoscope. Specifically, the first elevation range X may be the range up to the maximum elevation angle for which no load is placed on a mini-scope or the like, and the second elevation range Y may be the range up to the maximum elevation angle when a regular treatment instrument is used in the endoscope system of the fifth embodiment.

A conventional endoscope system is disadvantageous in that that considerable time is needed to wash and sterilize the system because a complicated structure in which the temporary locking member 100 is disposed inside the storage chamber 25 is brought into contact with the body or the like, and the intended functions cannot be obtained because of plugging and other undesirable phenomena brought about by inadequate washing, as described in Japanese Patent Application Laid-open No. 5-123290.

However, the endoscope system of the fifth embodiment can yield consistently stable effects without contamination of the temporary locking member 100, because the temporary locking member 100 is provided within the watertight/airtight space 92 free of contact with the body.

Because there is no change in the structure of the portions that come into contact with the body, the portions can be washed and sterilized in the conventional manner.

Furthermore, the endoscope system is effective in the sense that instruments can be readily exchanged because the temporary locking member 100 is fixed by a screw, and the operator can obtain the desired clicking sensation by using an elastic member 106 having a varying elastic force in the temporary locking member 100.

(Sixth Embodiment)

The endoscope system relating to the sixth embodiment of the present invention will next be described using FIGS. 31 through 35.

The sixth embodiment is designed to reliably guide the guidewire 56 to the guidewire catch groove 58 from the guide plane 29 of the treatment instrument elevator 27.

FIG. 31 depicts the previously described treatment instrument elevator 27.

The apex of the guide plane 29 of the treatment instrument elevator 27 has a guidewire catch groove 58 for securing solely the guidewire 56 by elevation. This guidewire catch groove 58 is formed in a substantial V-shape. The central axis M of the substantially V-shaped guidewire catch groove 58 in the threading direction of the treatment instrument is disposed along the same line as the central axis Mo in the treatment instrument threading direction of the guide plane 29 formed in a substantial V-shape.

Also, the guidewire catch groove 58 and guide plane 29 are formed so as to be connected by a guide surface 145, as depicted in FIG. 33.

Conventionally, the guidewire 56 is often oriented in a direction different from the central axis M of the guidewire catch groove 58 when protruding from the endoscope tip 17, as depicted in FIG. 32A.

The treatment instrument elevator 27 is gradually elevated to allow a guidewire 56 disposed out of alignment with the guidewire catch groove 58 to be fixed in the guidewire catch groove 58, whereby the guidewire is guided to the central axis Mo along the substantially V-shaped guide plane 29, the treatment instrument elevator 27 is elevated further, and the guidewire is guided towards the guidewire catch groove 58.

Figure 34A:
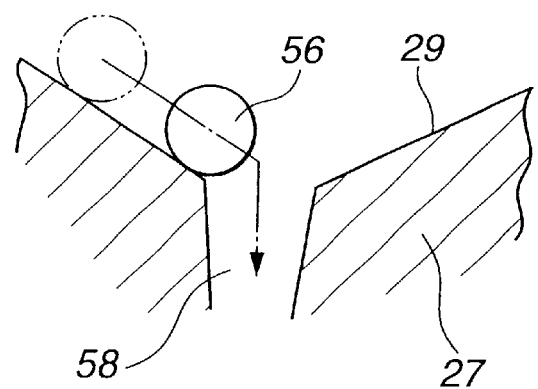
FIG. 34A is a diagram depicting the relation of the guide surface of the treatment instrument elevator in a conventional endoscope system with a guidewire.

In other words, the guidewire 56 of a conventional endoscope system is guided from the guide plane 29 of the treatment instrument elevator 27 towards the guidewire catch groove 58 by a process in which the treatment instrument elevator 27 is elevated and the guidewire 56 is eventually guided towards the guidewire catch groove 58 when the guidewire 56 begins to move towards the guidewire catch groove 58 from the guide plane 29, as depicted in FIG. 34A.

Consequently, the elevation angle of the treatment instrument elevator 27 increases in the conventional endoscope system because the guidewire 56 is out of alignment with the central axis Mo of the guide plane 29. There is also the risk that the guidewire 56 will be unable to be guided from the guide plane 29 to the guidewire catch groove 58 when considerably out of alignment with respect to the central axis Mo of the guide plane 29.

Figure 34B:
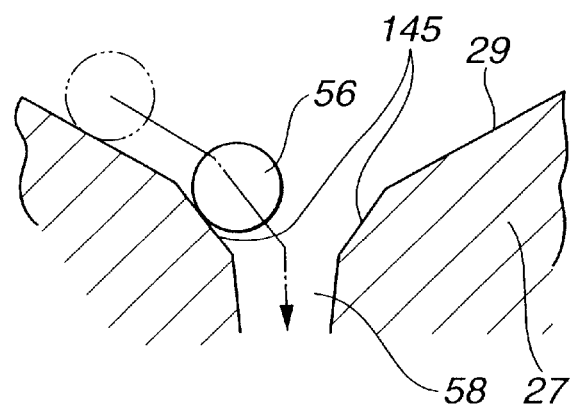
FIG. 34B is a diagram depicting the relation between the guidewire and the guide surface of the treatment instrument elevator in the endoscope system according to the sixth embodiment of the present invention.

By contrast, the endoscope system of the present invention is configured with a guide surface 145 that connects the guide plane 29 and the guidewire catch groove 58, as depicted in FIG. 34B. By this means, the guidewire 56 is guided along the guide plane 29 to the central axis Mo of the guide plane 29 when the treatment instrument elevator 27 is elevated as depicted in FIG. 32B. Because of the presence of the guide surface 145, the guidewire 56 thus guided is then directed to the guidewire catch groove 58 during the rapid step that precedes movement towards the guidewire catch groove 58.

In the endoscope system of the present invention, the guidewire 56 can thus be engaged in a rapid and reliable manner with the guidewire catch groove 58 when the guidewire 56 is guided to the guidewire catch groove 58 provided with a central axis M coaxial with the central axis Mo of the guide plane 29, and it is easier to exchange treatment instruments in which the guidewire 56 is used as a guide by gradually increasing the elevation angle of the treatment instrument elevator 27.

In other words, the endoscope system of the present invention is configured such that a guidewire 56 with an unstable direction can be rapidly guided towards the guidewire catch groove 58 from the guide plane 29 via the guide surface 145 when placed on the guide plane 29 in response to the elevation of the treatment instrument elevator 27, and the guidewire 56 can be locked and fixed in the guidewire catch groove 58 in a reliable manner.

A modification of the endoscope system relating to the sixth embodiment of the present invention will next be described using FIG. 35.

Figure 35:
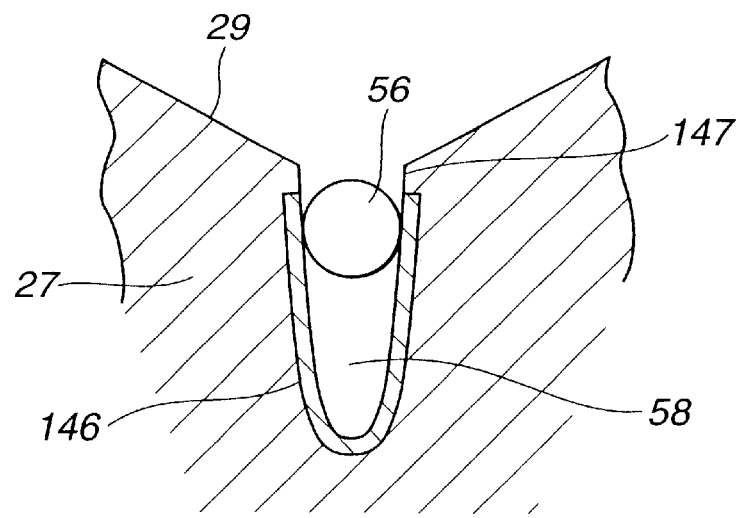
FIG. 35 is a diagram depicting a modification of the guide surface of the treatment instrument elevator in the endoscope system according to the sixth embodiment of the present invention.

The modification of the sixth embodiment is provided with a frictional resistance member 146 on the inner surface of the guidewire catch groove 58, as depicted in FIG. 35.

In the modification of the sixth embodiment, the guidewire 56 guided to the guidewire catch groove 58 by the guide plane 29 through the elevation of the treatment instrument elevator 27 is engaged by the frictional resistance member 146 provided to the inner surface of the guidewire catch groove 58, and is thus firmly engaged by the frictional resistance created by the frictional resistance member 146.

The frictional resistance member 146 is obtained by bonding (or embedding) a rubber member or other member of high frictional resistance with the aid of an adhesive or the like to the surface of the guidewire 56 in contact with the inner surface of the guidewire catch groove 58, or to the entire surface of the guidewire catch groove 58.

It is apparent in the present invention that embodiments differing across a wide range can be configured based on the present invention without deviating from the spirit or scope of the invention. The present invention is not restricted by the specific embodiments thereof, other than by the limits placed thereon according to the attached claims.

What is claimed is:

1. An endoscope system comprising:

an endoscope main body having an insertion portion in which a lumen is formed, the insertion portion having a proximal end and a distal end, a distal end opening of the lumen being provided to the distal end of the insertion portion, and a proximal end opening of the lumen being provided to the proximal end of the insertion portion;

a first fixing member provided to the distal end of the insertion portion, capable of selecting between a fixed state for fixing a distal end portion of a linear member inserted into the lumen and a released state thereof in the distal end of the insertion portion;

a second fixing member provided to the proximal end of the insertion portion, capable of selectively fixing a proximal end portion of the linear member inserted into the lumen in the proximal end of the insertion portion; and a tubular member having a proximal end, a distal end, and a lumen running therebetween, and removably inserted into the lumen, wherein a slit is formed from the proximal end of the tubular member towards the distal end thereof.

2. The endoscope system as claimed in claim 1, wherein the first fixing member comprises:

a guide member that is provided to the distal end of the endoscope main body insertion portion, is capable of guiding the distal end of the tubular member inserted into the lumen and protruding from the distal end opening and selectively changing the protruding direction of the distal end with respect to the insertion portion, the guide member having a guide surface for guiding the tubular member provided to the guide member; and a support portion provided in the vicinity of the distal end opening located opposite the guide surface in the fixing position of the guide member.

3. The endoscope system as claimed in claim 1, wherein the first fixing member is provided in the vicinity of the distal end opening of the lumen.

4. The endoscope system as claimed in claim 2, wherein the guide surface is formed with a groove in which the linear member is engaged.

5. The endoscope system as claimed in claim 2, wherein a notifying mechanism is provided to the endoscope main body for notifying the operator that the first fixing member has reached a fixed state from a released state.

6. The endoscope system as claimed in claim 3, wherein the distal end of the insertion portion is provided with a guide member for guiding the distal end portion protruding from the distal end opening of the tubular member inserted into the lumen, and selectively changing the protruding direction with respect to the insertion portion.

7. The endoscope system as claimed in claim 3, wherein the first fixing member comprises a loop-shaped snare for fixing the distal end portion of the linear member protruding from the distal end opening of the linear member.

8. The endoscope system as claimed in claim 3, wherein the first fixing member comprises a hook for fixing the distal end portion of the linear member protruding from the distal end opening of the linear member.

9. The endoscope system as claimed in claim 3, wherein the first fixing member comprises a linear member fixing member that is provided to the distal end portion of the insertion portion, and is capable of selectively traveling to a fixing position in which the linear member is fixed, and to a releasing position for releasing the fixing of the linear member.

10. The endoscope system as claimed in claim 4, wherein the groove is constituted by two mutually opposing wall surfaces with which the outer surface of the linear member makes contact when the linear member is fixed.

11. The endoscope system as claimed in claim 4, wherein the width of the groove formed in the guide surface is greater than the outside diameter of the linear member, and less than the outside diameter of the tubular member.

12. The endoscope system as claimed in claim 11, wherein the guide member is capable of traveling selectively between the guide position for changing the protruding direction of the tubular member and the fixing position for fixing the linear member; and a notifying mechanism is provided to the endoscope main body for notifying the operator that the guide member has traveled to the fixing position.

13. The endoscope system as claimed in claim 12, wherein the width in the axial direction of the slit formed in the tubular member is less than the outside diameter of the linear member.

14. The endoscope system as claimed in claim 13, wherein the center of the groove in the axial direction of the insertion portion is substantially the same as the center of the guide surface in the axial direction of the insertion portion.

15. An endoscope system comprising:

an endoscope main body having an insertion portion with a lumen formed therein, the lumen having a distal end opening at a distal end of the insertion portion and a proximal end opening in a proximal end of the insertion portion;

a guidewire removably inserted into the lumen;

a first fixing member that is provided in the vicinity of the distal end opening of the lumen in the distal end of the insertion portion, and is capable of selectively fixing the guidewire inserted into the lumen in the vicinity of the distal end opening;

a second fixing member that is provided in the vicinity of the proximal end opening of the lumen in the proximal end of the insertion portion, and is capable of selectively fixing the guidewire inserted into the lumen in the vicinity of the proximal end opening; and a treatment instrument releasably inserted into the lumen, having a proximal end, a distal end, and a lumen running therebetween, the treatment instrument being provided with a slit extending from the proximal end to a middle portion thereof, the slit being formed along an axial direction of the treatment instrument.

16. The endoscope system as claimed in claim 15, wherein the first fixing member comprises:

a treatment instrument elevator having a first elevation range for elevating the treatment instrument inserted into the lumen, and a second elevation range for fixing the guidewire, the treatment instrument elevator being provided with a guide surface for guiding the treatment instrument; and a support portion provided in the vicinity of the distal end opening located opposite the guide surface in the second elevation range of the treatment instrument elevator.

17. The endoscope system as claimed in claim 16, wherein the treatment instrument elevator is provided with a guide portion that guides the treatment instrument, and a groove for engaging the guidewire is formed on the guide portion.

18. The endoscope system as claimed in claim 17, wherein a notifying mechanism is provided to the endoscope main body for notifying the operator that the treatment instrument elevator is in the second elevation range.

19. The endoscope system as claimed in claim 18, wherein the center of the groove in the axial direction of the insertion portion is substantially the same as the center of the guide surface in the axial direction of the insertion portion.

20. An endoscope system comprising:

an endoscope main body having an insertion portion in which a lumen is formed, the insertion portion having a proximal end and a distal end, a distal end opening of the lumen being provided to the distal end of the insertion portion, and a proximal end opening of the lumen being provided to the proximal end of the insertion portion;

a treatment instrument releasably inserted into the lumen, having a proximal end, a distal end, and a lumen running therebetween, and being provided with a slit formed from the proximal end towards the terminal end thereof;

a first fixing member provided to the distal end of the insertion portion and being designed for fixing the distal end of a guidewire inserted into the lumen, the first fixing member being provided to the distal end of the insertion portion, and comprising a treatment instrument elevator having a guide portion for guiding a treatment instrument inserted into the lumen, and a support portion provided, at the vicinity of the distal end opening of the lumen, in a location opposite the guide portion when the treatment instrument elevator is elevated; and a second fixing member provided to the proximal end of the insertion portion, and being capable of selectively fixing the proximal end of the guidewire inserted into the lumen.

21. An endoscope system comprising:

an endoscope main body having an insertion portion in which a lumen is formed, the insertion portion having a proximal end and a distal end, a distal end opening of the lumen being provided to the distal end of the insertion portion, and a proximal end opening of the lumen being provided to the proximal end of the insertion portion;

a treatment instrument releasably inserted into the lumen, the treatment instrument having proximal end, a distal end, and a lumen running therebetween, and being provided with a slit formed from the proximal end towards the terminal end thereof;

a first fixing member provided to the distal end of the insertion portion and designed for fixing the distal end of a guidewire inserted into the lumen, the first fixing member being provided to the distal end of the insertion portion, and comprising a treatment instrument elevator having a guide portion for guiding a treatment instrument inserted into the lumen, and a support portion provided, at the vicinity of the distal end opening of the lumen, in a location opposite the guide portion when the treatment instrument elevator is elevated, the treatment instrument elevator having a first elevation range and a second elevation range, and the guidewire being fixed in the second elevation range; and a second fixing member provided to the proximal end of the insertion portion, the second fixing member being capable of selectively fixing the proximal end of the linear member inserted into the lumen.

22. The endoscope system as claimed in claim 21, further comprising notifying mechanism provided to the endoscope main body for notifying the operator that the treatment instrument elevator is in the second elevation range.

23. An endoscope system comprising:

an endoscope main body having an insertion portion in which a lumen is formed, the insertion portion having a proximal end and a distal end, a distal end opening of the lumen being provided to the distal end of the insertion portion, and a proximal end opening of the lumen being provided to the proximal end of the insertion portion;

an urging member provided to the distal end of the insertion portion, capable of travel between an urging position for urging a distal end of a linear member inserted into the lumen in the vicinity of a lumen opening, and a releasing position for releasing the urging of the linear member, a relative displacement of the linear member with respect to the insertion portion being restricted in the urging position of the urging member;

a distal end fixing member provided to the proximal end of the insertion portion, and being capable of selectively fixing a proximal end of the linear member inserted into the lumen; and a tubular member having a proximal end, a distal end, and a lumen running therebetween, being removably inserted into the lumen, a slit being formed from the proximal end of the tubular member towards the distal end thereof.

24. The endoscope system as claimed in claim 23, wherein the urging member comprises:

a guide member provided to the distal end of the endoscope main body insertion portion, and being capable of guiding the distal end of the tubular member inserted into the lumen and protruding from the distal end opening, the guide member selectively changing the protruding direction of the distal end with respect to the insertion portion, and being provided with a guide surface for guiding the tubular member.

25. The endoscope system as claimed in claim 23, wherein the urging member is provided in the vicinity of the distal end opening of the lumen.

26. The endoscope system as claimed in claim 25, wherein a groove for engaging the linear member is provided in the guide surface.

27. The endoscope system as claimed in claim 25, wherein the endoscope main body is provided with a notifying mechanism for notifying the operator that the urging member is in the urging position for urging the linear member in the vicinity of the edge of the lumen.

28. The endoscope system as claimed in claim 25, wherein the urging member comprises a loop-shaped snare for fixing the distal end portion protruding from the distal end opening of the linear member inserted into the lumen.

29. The endoscope system as claimed in claim 25, wherein the urging member comprises a hook for fixing the distal end portion protruding from the distal end opening of the linear member inserted into the lumen.

30. The endoscope system as claimed in claim 25, wherein the urging member comprises a linear member urging member capable of selectively traveling between an urging position for urging the linear member against the inner circumferential surface of the lumen, and an urging releasing position for releasing the urging of the linear member, the linear member urging member being provided to the distal end of the insertion portion.

31. The endoscope system as claimed in claim 26, wherein the groove formed in the guide surface is provided with a tapered surface.

32. The endoscope system as claimed in claim 26, wherein the width of the groove formed in the guide surface is greater than the outside diameter of the linear member, and less than the outside diameter of the tubular member.

33. The endoscope system as claimed in claim 32, wherein the guide member is capable of selectively traveling between a guide position for guidance of the tubular member, and a fixing position for fixing the linear member; and the endoscope main body is provided with a notifying mechanism for notifying the operator that the guide member has traveled to the fixing position.

34. The endoscope system as claimed in claim 33, wherein the width of the slit formed in the tubular member in the axial direction thereof is less than the outside diameter of the linear member.

35. The endoscope system as claimed in claim 34, wherein the center of the groove in the axial direction of the insertion portion is substantially the same as the center of the guide surface in the axial direction of the insertion portion.

36. A medical treatment method comprising:

inserting a first treatment instrument into a lumen of an endoscope insertion portion and placing a distal end of a first treatment instrument in a body cavity;

placing a guidewire in the lumen of the first treatment instrument;

pulling a proximal end of the guidewire diametrically from the lumen of the first treatment instrument after a distal end of the guidewire inserted into the first treatment instrument is placed in the body cavity;

fixing a portion of the proximal end of the guidewire pulled from the first treatment instrument at a proximal end of the lumen of the endoscope insertion;

pulling the first treatment instrument towards a proximal end of the insertion portion;

fixing the distal end of the guidewire at a distal end of the endoscope insertion portion after a distal end of the first treatment instrument is positioned within the insertion portion of the endoscope;

releasing the fixing of the guidewire in the proximal end of the endoscope insertion portion; and pulling the first treatment instrument from a proximal end opening of the endoscope insertion portion.

37. The treatment method as claimed in claim 36, wherein the distal end portion of the guidewire is fixed by using a treatment instrument elevator.

38. The treatment method as claimed in claim 37, wherein the treatment instrument elevator has a first elevation range and a second elevation range, and the guidewire is fixed in the second elevation range.

39. The medical treatment method as claimed in claim 36, further comprising:

inserting the guidewire into the lumen provided to the second treatment instrument, and inserting the second treatment instrument into the lumen of the endoscope insertion portion;

pulling the proximal end portion of the guidewire inserted in the lumen of the second treatment instrument diametrically from the lumen of the second treatment instrument;

fixing the proximal end portion of the guidewire in the proximal end of the endoscope;

inserting the second treatment instrument; and releasing the fixing in the distal end of the endoscope insertion portion, and further inserting the second treatment instrument.

40. An endoscope system comprising:

an endoscope main body having an insertion portion, which has a proximal end, a distal end, and a lumen running therebetween;

a first fixing means provided to the distal end of the insertion portion of the endoscope for fixing a linear member inserted into the lumen in the distal end;

a second fixing means provided to the proximal end of the insertion portion of the endoscope for fixing a linear member inserted into the lumen in the proximal end; and a tubular member that has a proximal end, a distal end, and a lumen running therebetween, is removably inserted into the lumen, and is provided with a slit formed from the proximal end of the tubular member towards the distal end thereof.

* * * * *